US008143221B2

(12) United States Patent
Gozes et al.

(10) Patent No.: US 8,143,221 B2
(45) Date of Patent: *Mar. 27, 2012

(54) USE OF ADNF POLYPEPTIDES FOR TREATING PERIPHERAL NEUROTOXICITY

(75) Inventors: Illana Gozes, Ramat-Hasharon (IL); James Miller, Vancouver (CA)

(73) Assignees: Ramot at Tel-Aviv University, Tel Aviv (IL); Allon Therapeutics, inc., Vancouver, B.C. (CA)

(*) Notice: Subject to any disclaimer, the term of this patent is extended or adjusted under 35 U.S.C. 154(b) by 179 days.

This patent is subject to a terminal disclaimer.

(21) Appl. No.: 12/245,517

(22) Filed: Oct. 3, 2008

(65) Prior Publication Data

US 2009/0137469 A1    May 28, 2009

Related U.S. Application Data

(62) Division of application No. 11/388,634, filed on Mar. 23, 2006, now Pat. No. 7,452,867.

(60) Provisional application No. 60/664,908, filed on Mar. 23, 2005.

(51) Int. Cl.
*A61K 38/08* (2006.01)
*A61K 38/10* (2006.01)

(52) U.S. Cl. ............ 514/18.2; 514/17.7; 514/19.2; 514/19.3; 514/21.4; 514/21.5; 514/21.6; 514/21.7

(58) Field of Classification Search ............ None
See application file for complete search history.

(56) References Cited

U.S. PATENT DOCUMENTS

| | | | |
|---|---|---|---|
| 4,587,046 A | 5/1986 | Goodman et al. | |
| 5,198,420 A | 3/1993 | Donahoe et al. | |
| 5,556,757 A | 9/1996 | Alstyne et al. | |
| 5,767,240 A | 6/1998 | Brenneman et al. | |
| 6,113,947 A | 9/2000 | Cleland et al. | |
| 6,174,862 B1 | 1/2001 | Brenneman | |
| 6,613,740 B1 | 9/2003 | Gozes et al. | |
| 6,649,411 B2 | 11/2003 | Gozes et al. | |
| 6,890,904 B1* | 5/2005 | Wallner et al. | 514/14 |
| 6,933,277 B2 | 8/2005 | Brenneman et al. | |
| 7,264,947 B2 | 9/2007 | Gozes et al. | |
| 7,384,908 B1 | 6/2008 | Brenneman et al. | |
| 7,427,590 B2 | 9/2008 | Brenneman et al. | |
| 7,427,598 B2 | 9/2008 | Spong et al. | |
| 7,452,867 B2* | 11/2008 | Gozes et al. | 514/12 |
| 7,863,247 B1 | 1/2011 | Brenneman et al. | |
| 2002/0111301 A1 | 8/2002 | Brenneman et al. | |
| 2003/0036521 A1* | 2/2003 | Gozes et al. | 514/44 |
| 2003/0166544 A1 | 9/2003 | Clark et al. | |
| 2004/0053313 A1 | 3/2004 | Gozes et al. | |
| 2007/0054847 A1 | 3/2007 | Gozes et al. | |
| 2008/0194488 A1 | 8/2008 | Gozes et al. | |
| 2009/0124543 A1 | 5/2009 | Gozes et al. | |
| 2009/0170780 A1 | 7/2009 | Gozes et al. | |
| 2009/0203615 A1 | 8/2009 | Spong et al. | |
| 2009/0247457 A1 | 10/2009 | Brenneman et al. | |
| 2010/0216723 A1 | 8/2010 | Gozes et al. | |

FOREIGN PATENT DOCUMENTS

| | | |
|---|---|---|
| EP | 1 206 489 B1 | 5/2004 |
| WO | WO 92/18140 A1 | 10/1992 |
| WO | WO 96/11948 A1 | 4/1996 |
| WO | WO 98/35042 A1 | 8/1998 |
| WO | WO 00/27875 A2 | 5/2000 |
| WO | WO 00/53217 A2 | 9/2000 |
| WO | WO 01/12654 A2 | 2/2001 |
| WO | WO 01/92333 A2 | 2/2001 |
| WO | WO 01/92333 A2 | 12/2001 |
| WO | WO 2004/080957 A2 | 9/2004 |

OTHER PUBLICATIONS

Bassan, M. et al. "VIP-Induced Mechanism of Neuroprotection: The Complete Sequence of a Femtomolar-Acting Activity-Dependent Neuroprotective Protein." *Regulatory Peptides*, vol. 71, No. 2, (Aug. 15, 1997).
Bedikian, Agop Y., et al., "Phase II Trial of Docetaxel in Patients with Advanced Cutaneous Malignant Melanoma Previously Untreated with Chemotherapy;" Dec. 1995; Journal of Clinical Oncology; Vo. 13; No. 12; pp. 2895-2899.
Bassan, M. et al. "Complete Sequence of a Novel Protein Containing a Femtomolar-Activity-Dependent Neuroprotective Peptide." *Journal of Neurochemistry*, vol. 72, pp. 1283-1293 (1999).
Beni-Adani, L. et al. "Activity-Dependent Neurotrophic Protein is Neuroprotective in a Mouse Model of Closed Head Injury." Society for Neuroscience, 28th Annual Meeting, Los Angeles, CA, Nov. 7-12, 1998. *Abstracts*, vol. 23, Part 1, p. 1043 (1998).
Brenneman, D.C. and Gozes, I. "A Femtomolar-Acting Neuroprotective Peptide." *Journal of Clinical Investigation*, vol. 97, pp. 2299-2307 (1996).
Brenneman et al. "Neuronal Cell Killing by the Envelope Protein of HIV and Its Prevention by Vasoactive Intestinal Peptide." *Nature* 335:636 (1988).
Brenneman et al. "*N*-Methyl-D-Aspartate Receptors Influence Neuronal Survival in Developing Spinal Cord Cultures" *Dev. Brain Res.* 51:63 (1990).
Brenneman, D.E. et al. "Identification of a Nine Amino Acid Core Peptide from Activity Dependent Neurotrophic Factor I." Society for Neuroscience, 27th Annual Meeting, New Orleans, LA, Oct. 25-30, 1997. *Abstracts*, vol. 23, Part 2, p. 2250 (1997).
Brenneman, D.E. et al. "Activity-Dependent Neurotrophic Factor: Structure-Activity Relationships of Femtomolar-Acting Peptides." *Journal of Pharmacology and Experimental Therapeutics*, vol. 285, pp. 619-627 (1998).
Brenneman, D.E., et al.; "Protective Peptides Derived from Novel Glial Proteins;" 2000; Biochemical Society Transactions; vol. 28; Part 4; pp. 452-455.

(Continued)

*Primary Examiner* — Jeffrey E Russel
(74) *Attorney, Agent, or Firm* — Kilpatrick Townsend & Stockton LLP

(57) ABSTRACT

This invention relates to the use of ADNF polypeptides in the treatment of neurotoxicity induced by chemical agents or by disease processes. The ADNF polypeptides include ADNF I and ADNF III (also referred to as ADNP) polypeptides, analogs, subsequences such as NAP and SAL, and D-amino acid versions (either wholly D-amino acid peptides or mixed D- and L-amino acid peptides), and combinations thereof which contain their respective active core sites.

21 Claims, 9 Drawing Sheets

OTHER PUBLICATIONS

Chiba, Tomohiro et al.; "Neuroprotective Effect of Activity-Dependent Neurotrophic Factor Against Toxicity From Familial Amyotrophic Lateral Sclerosis-Linked Mutant SOD1 in Vitro and in Vivo"; 2004, *Journal of Neuroscience Research*, vol. 78, pp. 542-552.

Chiba, Tomohiro, et al., "Development of a Femtomolar-Acting Humanin Derivative Named Colivelin by Attaching Activity-Dependent Neurotropic Factor to its N Terminus: Characterization of Colivelin-Mediated Neuroprotection against Alzheimer's Disease-Relevant Insults in Vitro and In Vivo;" Nov. 2, 2005; *The Journal of Neuroscience*; vol. 25; No. 44; pp. 10252-10261.

Davidson, A. et al. "Protection Against Developmental Retardation and Learning Impairments in Apolipoprotein E-Deficient Mice by Activity-Dependent Femtomolar-Acting Peptides." Society for Neuroscience, 27th Annual Meeting, New Orleans, LA, Oct. 25-30, 1997. *Abstracts*, vol. 23, Part 2, p. 2250 (1997).

Dibbern, D.A., Jr. et al. "Inhibition of Murine Embryonic Growth by Human Immunodeficiency Virus Envelope Protein and Its Prevention by Vasoactive Intestinal Peptide and Activity-Dependent Neurotrophic Factor." *Journal of Clinical Investigation*, vol. 99, pp. 28377-2841 (1997).

Divinski, Inna, et al ., "A Femtomolar Acting Octapeptide Interacts with Tubulin and Protecots Astrocytes Against Zinc Intoxication;" The Journal of Biological Chemistry; Jul. 2, 2004; vol. 279, No. 27; pp. 28531-28538.

Furman, Sharon, et al.; "Subcellular Localization and Secretion of Activity-Dependent Neuroprotective Protein in Astrocytes;" 2004; Neuron Gilia Biology; vol. 1; pp. 193-199.

GenBank Accession No. AB018327 from the DNA Data Bank of Japan (DDBJ) (released Nov. 17, 1998).

Giladi, E. "Protection Against Developmental and Learning Impairments in Apolipoprotein E-Deficient Mice by Activity-Dependent Femtomolar-Acting Peptides." *Neuroscience Letters*, Supplement 48 S1-S60, P. S19 (1997).

Glazner, G.W. et al. "A 9 Amino Acid Peptide Fragment of Activity-Dependent Neurotrophic Factor (ADNF) Protects Neurons from Oxidative Stress-Induced Death." Society for Neuroscience, 27th Annual Meeting, New Orleans, LA, Oct. 25-30, 1997. *Abstracts*, vol. 23, Part 2, p. 2249 (1997).

Glazner, G.W. et al. "Activity Dependent Neurotrophic Factor: A Potent Regulator of Embryonic Growth." *Anat. Embryol.* 200:65-71 (1999).

Gozes, I. and Brenneman, D.E. "Activity-Dependent Neurotrophic Factor (ADNF)." *Journal of Molecular Neuroscience*, vol. 7, pp. 235-244 (1996).

Gozes, I. et al. "Stearyl-Norleucine-Vasoactive intestinal Peptide (VIP): A novel VIP Analog for Noninvasive Impotence Treatment." *Endocrinology*, vol. 134, pp. 2125 (1994).

Gozes, I. et al. "Superactive Lipophilic Peptides Discriminate Multiple Vasoactive intestinal Peptide Receptors." *Journal of Pharmacology and Experimental Therapeutics*, vol. 273, pp. 161-167 (1995).

Gozes, I. et al. "Neuroprotective Strategy for Alzheimer Disease: Intranasal Administration of a Fatty Neuropeptide." *Proc. Natl. Acad. Sci. USA*, vol. 93, pp. 427-432 (1996).

Gozes I. et al. "Antiserum to Activity-Dependent Neurotrophic Factor Produces Neuronal Cell Death in CNS Cultures: Immunological and Biological Specificity." *Developmental Brain Research*, vol. 99, pp. 167-175 (1997).

Gozes, I. et al. A Femtomolar-Acting Activity-Dependent Neuroprotective Protein (ADNP). *Neuroscience Letters*, Supplement 48 S1-S60, p. S21 (1997).

Gozes, I. et al. "Protection Against Developmental Retardation in Apolipoprotein E-Deficient Mice by a Fatty neuropeptide: Implications for Early Treatment of Alzheimer's Disease." *Journal of Neurobiology*, vol. 33, pp. 329-342 (1997).

Gozes, I. et al. "The cDNA Structure of a Novel Femtomolar-Acting Neuroprotective Protein: Activity-Dependent-Neurotrophic Factor III (ADNFIII)." Society for Neuroscience, 27th Annual Meeting, New Orleans, LA, Oct. 25-30, 1997. *Abstracts*, vol. 23, Part 2, p. 2250 (1997).

Gozes, et al., "A Novel Signaling Molecule for Neuropeptide Action: Activity-dependent Neuroprotective Protein"; Annals of the New York Academy of Sciences, 897:125-135 (1999).

Gozes, I. et al. "Activity-dependent neurotrophic factor: Intranasal administration of femtomolar-acting peptides improve performance in a water maze" *Journal of Pharmacology and Experimental Therapeutics*, vol. 293, pp. 1091-1098 (2000).

Gozes, Illana, "Tubulin in the Nervous System;" 1982; Neurochemistry International; vol. 4; No. 23; pp. 101-120.

Gozes, Illana and Divinski, Inna; "The Femtomolar-Acting NAP Interacts with Microtubules: Novel Aspects of Astrocyte Protection;" 2004; Journal of Alheimer's Disease; vol. 6; pp. S37-S41.

Gozes, Illana; "Tau as a Drug Target in Alzheimer's Diseaase;" 2002; Journal of Molecular Neuroscience; vol. 19; pp. 337-338.

Gozes, Illana, et al.; "From Vasoactive Intestinal Peptide (VIP) Through Activity-Dependent Neuroprotective Protein (ADNP) to NAP;" 2003; Journal of Molecular Neuroscience; vol. 20; pp. 315-322.

Gressens, P. et al. "Growth Factor Function of Vasoactive Intestinal Peptide in Whole Cultured Mouse Embryos." *Nature* 362:155-58 (1993).

Hannigan, J.H. and Berman, R.F. "Amelioration of Fetal Alcohol-Related Neurodevelopmental Disorders in Rats: Exploring Pharmacological and Environmental Treatments." *Neurotoxicol. & Teratol.* 22(1):103-111 (2000).

Hausheer et al., "Diagnosis, Management, and Evaluation of Chemotherapy-Induced Peripheral Neuropathy," *Semin. Oncol.* 33:15-49 (2006).

Hill, J.M. et al. "Learning Impairment in Adult Mice Produced by Early Embryonic Administration of Antiseum to Activity-Dependent Neurotrophic Factor (ADNF)." Society for Neuroscience, 27th Annual Meeting, New Orleans, LA, Oct. 25-30, 1997. *Abstracts*, vol. 23, Part 2, p. 2250 (1997).

Lagreze, Wolf A., et al.; "The Peptides ADNF-9 and NAP Increase Survival and Neurite Outgrowth of Rat Retinal Ganglion Cells in Vitro;" Mar. 2005; Investigative Opthalmology & Visual Science; vol. 46; No. 3; pp. 933-938.

Lee, Virginia M.-Y., et al., "Transgenic Animal Models of Taupathies;" 2005; Biochimica et Biophysica Acta; vol. 1739; pp. 251-259.

Lilling, G. et al. "Inhibition of Human Neuroblastoma Growth by a Specific VIP Antagonist." *Journal of Molecular Neuroscience*, vol. 5, pp. 231-239 (1995).

Mahato et al. "Development of Targeted Delivery Systems for Nucleic Acid Drugs." *J. of Drug Targeting* 4(6):337-357 (1997) [Abstract].

McKune, S.K. et al. "Localization of mRNA for Activity-Dependent Neurotrophic Factor III (ADNF III) in mouse Embryo and Adult CNS." Society for Neuroscience, 27th Annual Meeting, New Orleans, LA, Oct. 25-30, 1997. Abstracts, vol. 23, Part 2, p. 2249 (1997).

Nagase, et al, "Prediction of the Coding Sequences of Unidentified Human Genes. XI. The Complete Sequences of 100 New cDNA Clones from Brain Which Code for Large Proteins in vitro"; DNA Research 5:5:277-286 (1998).

Nelbock, P. et al. A cDNA for a Protein that Interacts with the Human Immunodeficiency Virus Tat Transactivator. *Science*, vol. 248, pp. 1650-1653 (1990).

Oberdoester, J. et al. "The Effects of Ethanol on Neuronal Cell Death: Implication for the Fetal Alcohol Syndrome." *FASEB Journal* 12(4):A134 (Mar. 17, 1998).

Pelsman, A. et al. "In Vitro Degeneration of Down Syndrome neurons is Prevented by Activity-Dependent Neurotrophic Factor-Derived Peptides." Society for Neuroscience, 28th Annual Meeting, Los Angeles, CA, Nov. 7-12, 1998. *Abstracts*, vol. 24, p. 1044 (1998).

Skolnick, J. and Fetrow, J.S. "From Genes to Protein Structure and Function: Novel Applications of Computational Approaches in the Genomic Era." *Trends in Biotech.* 18(1):34-39 (2000).

Smith, A.E. "Viral Vectors in Gene Therapy." *Ann. Rev.Microbiol.* 49:807-838 (1995) [Abstract].

Smith-Swintosky, Virginia L., et al., "Activity-Dependent Neurotrophic Factor-9 and NAP Promote Neurite Outgrowth in Rat Hippocampal and Cortical Cultures;" 2005, Journal of Molecular Neuroscience; vol. 25; pp. 225-237.

Spinney, L. "New Peptides Prevent Brain Damage." *Molecular Medicine Today* 5(7):282 (Jul. 1999).

Spong et al. "Prevention of Fetal Alcohol Syndrome by Novel Peptides." *FASEB Journal* 13(5):A881 (Mar. 15, 1991).

Spong et al. "Prevention of Fetal Demise and Growth Restriction in a Mouse Model of Fetal Alcohol Syndrome" *The Journal of Pharmacology and Experimental Therapeutics* 297:774-779 (2001).

Stillman and Cata, "Management of Chemotherapy-Induced Peripheral Neuropathy," *Curr. Pain Headache Rep.* 10:279-287, abstract only (2006).

Van Gool, S.W., et al.; "Disease-and Treatment-Related Elevation of the Neurodegenerative Market Tau in Children with Hematological Malignancies;" Leukemia; vol. 14; pp. 2076-2084.

Voet et al. *Biochemistry, 2nd Ed.*, p. 67.

Wilkemeyer et al. "Differential effects ethanol antagonism and neuroprotection in peptide fragment NAPVSIPQ prevention of ethanol-induced development toxicity" *PNAS* 100:8543-8548 (2003).

Zemlyak, Ilona, et al.; "A Novel Peptide Prevents Death in Enriched Neuronal Cultures;" 2000; Regulatory Peptides; vol. 96; pp. 39-43.

\* cited by examiner

Point 1 = water (ddw) trial 3; Point 2 = Odor #1, trial #1; Point 3 = Odor #1, trial 3; Point 4 = Odor #2, trial 1

* P<0.05, control and vincristine + NAP as compared to vincristine alone

USE OF ADNF POLYPEPTIDES FOR TREATING PERIPHERAL NEUROTOXICITY

CROSS-REFERENCES TO RELATED APPLICATIONS

This application is a divisional of U.S. application Ser. No. 11/388,634, filed Mar. 23, 2006 which claims the benefit of U.S. Provisional Application No. 60/664,908, filed Mar. 23, 2005; which is herein incorporated by reference for all purposes.

FIELD OF INVENTION

This invention relates to the use of ADNF polypeptides in the treatment of neurotoxicity. The present invention also relates to the manufacture of medicaments, methods of formulation and uses thereof. The ADNF polypeptides include ADNF I and ADNF III (also referred to as ADNP) polypeptides, analogs, subsequences such as NAP and SAL (defined below), and D-amino acid versions (either wholly D-amino acid peptides or mixed D- and L-amino acid peptides), and combinations thereof which contain their respective active core sites.

BACKGROUND OF THE INVENTION

NAP, an 8-amino acid peptide (NAPVSIPQ=Asn-Ala-Pro-Val-Ser-Ile-Pro-Gln); SEQ ID NO:2), is derived from a novel protein, activity-dependent neuroprotective protein, ADNP (U.S. Pat. No. 6,613,740, Bassan et al., *J. Neurochem.* 72: 1283-1293 (1999); Zamostiano, et al., *J. Biol. Chem.* 276: 708-714 (2001)). The NAP sequence within the ADNP gene is identical in rodents and humans (U.S. Pat. No. 6,613,740, Zamostiano, et al., *J. Biol. Chem.* 276:708-714 (2001)).

In cell cultures, NAP has been shown to have neuroprotective activity on cells of the central nervous system (CNS) at femtomolar concentrations (Bassan et al., 1999; Offen et al., *Brain Res.* 854:257-262 (2000)). Several animal models have also demonstrated NAP activity on diseases of the CNS. In animal models simulating parts of the Alzheimer's disease pathology, NAP was protective (Bassan et al., 1999; Gozes et al., *J. Pharmacol. Exp. Ther.* 293:1091-1098 (2000); see also U.S. Pat. No. 6,613,740). In normal aging rats, intranasal administration of NAP improved performance in the Morris water maze. (Gozes et al., *J. Mol. Neurosci.* 19:175-178 (2002). NAP reduced infarct volume and motor function deficits *Mol. Neurosci.* 19:175-178 (2002). NAP reduced infarct volume and motor function deficits after ischemic injury, by decreasing apoptosis (Leker et al., *Stroke* 33:1085-1092 (2002)) and reducing damage caused by closed head injury in mice by decreasing inflammation (Beni Adani et al., *J. Pharmacol. Exp. Ther.* 296:57-63 (2001); Romano et al., *J. Mol. Neurosci.* 18:37-45 (2002); Zaltzman et al., *NeuroReport* 14:481-484 (2003)). NAP has been shown to provide protective intervention in a model of fetal alcohol syndrome, reducing fetal demise and growth restrictions. (Spong et. al., *J Pharmacol Exp Ther.* 297:774-9 (2001)). Additionally, long term nasal NAP application in mice resulted in decreased anxiety (Alcalay et al., *Neurosci Lett.* 361(1-3):128-31 (2004)).

SAL, a 9-amino acid peptide (SALLRSIPA=Ser-Ala-Leu-Leu-Arg-Ser-Ile-Pro-Ala); (SEQ ID NO:1), also known as ADNF-9, was identified as the shortest active form of ADNF (see U.S. Pat. No. 6,174,862). SAL has been shown in in-vitro assays and in vivo disease models to keep neurons of the central nervous system alive in response to various insults (e.g. Gozes et al., 2000, infra; Brenneman et al., 1998. *J. Pharmacol. Exp. Ther.* 285, 619-627). D-SAL is an all D-amino acid derivative of SAL that is stable and orally available (Brenneman, et al., *J Pharmacol Exp Ther.* 309: 1190-7 (2004)) and surprisingly exhibits similar biological activity (potency and efficacy) to SAL in the systems tested.

ADNF polypeptides, including NAP and SAL, and uses thereof in neuroprotection against disorders of the central nervous system, are the subject of patents and patent applications including PCT WO 1/92333; U.S. Ser. No. 07/871, 973 filed Apr. 22, 1992, now U.S. Pat. No. 5,767,240; U.S. Ser. No. 08/342,297, filed Oct. 17, 1994 (published as WO96/11948), now U.S. Pat. No. 6,174,862; U.S. Ser. No. 60/037, 404, filed Feb. 7, 1997 (published as WO98/35042); U.S. Ser. No. 09/187,330, filed Nov. 11, 1998 (published as WO00/27875); U.S. Ser. No. 09/267,511, filed Mar. 12, 1999 (published as WO00/53217); U.S. Pat. No. 6,613,740, U.S. Ser. No. 60/149,956, filed Aug. 18, 1999 (published as WO01/12654); U.S. Ser. No. 60/208,944, filed May 31, 2000; and U.S. Ser. No. 60/267,805, filed Feb. 8, 2001; PCT/IL2004/000232, filed Mar. 11, 2004 (published as WO 2004/080957) herein each incorporated by reference in their entirety.

This disclosure provides new and surprising uses for ADNF polypeptides, including, e.g., NAP, SAL, D-NAP and D-SAL, in the treatment of neurotoxicity in the peripheral nervous system.

BRIEF SUMMARY OF THE INVENTION

In one aspect, the present invention provides a method for treating peripheral neurotoxicity in a subject, the method comprising administering a therapeutically effective amount of an ADNF polypeptide to a subject in need thereof.

In one embodiment, the ADNF polypeptide is a member selected from the group consisting of:
  (a) an ADNF I polypeptide comprising an active core site having the following amino acid sequence: Ser-Ala-Leu-Leu-Arg-Ser-Ile-Pro-Ala (SEQ ID NO:1), or an analogue thereof;
  (b) an ADNF III polypeptide comprising an active core site having the following amino acid sequence: Asn-Ala-Pro-Val-Ser-Ile-Pro-Gln (SEQ ID NO:2), or an analogue thereof, and
  (c) a mixture of the ADNF I polypeptide of part (a) and the ADNF III polypeptide of part (b), or their respective analogues.

In another embodiment, the ADNF polypeptide is a member selected from the group consisting of a full length ADNF I polypeptide, a full length ADNF III polypeptide (ADNP), and a mixture of a full length ADNF I polypeptide and a full length ADNF III polypeptide.

In one embodiment, the ADNF polypeptide is prepared by recombinant DNA methodology. In another embodiment, the active core site of the ADNF polypeptide comprises at least one D-amino acid. In another embodiment, the active core site of the ADNF polypeptide comprises all D-amino acids.

In one embodiment, the ADNF I polypeptide has the formula (R1)x-Ser-Ala-Leu-Leu-Arg-Ser-Ile-Pro-Ala-(R2)y (SEQ ID NO:20), or an analogue thereof, in which
  R1 is an amino acid sequence comprising from 1 to about 40 amino acids wherein each amino acid is independently selected from the group consisting of naturally occurring amino acids and amino acid analogs;
  R2 is an amino acid sequence comprising from 1 to about 40 amino acids wherein each amino acid is independently selected from the group consisting of naturally occurring amino acids and amino acid analogs; and
  x and y are independently selected and are equal to zero or one.

In one embodiment, the ADNF I polypeptide is selected from the group consisting of:

```
                                           (SEQ ID NO: 3)
Val-Leu-Gly-Gly-Gly-Ser-Ala-Leu-Leu-Arg-Ser-Ile-
Pro-Ala;

(SEQ ID NO: 4)
Val-Glu-Glu-Gly-Ile-Val-Leu-Gly-Gly-Gly-Ser-Ala-
Leu-Leu-Arg-Ser-Ile-Pro-Ala;

(SEQ ID NO: 5)
Leu-Gly-Gly-Gly-Ser-Ala-Leu-Leu-Arg-Ser-Ile-Pro-
Ala;

(SEQ ID NO: 6)
Gly-Gly-Gly-Ser-Ala-Leu-Leu-Arg-Ser-Ile-Pro-Ala;

(SEQ ID NO: 7)
Gly-Gly-Ser-Ala-Leu-Leu-Arg-Ser-Ile-Pro-Ala;

(SEQ ID NO: 8)
Gly-Ser-Ala-Leu-Leu-Arg-Ser-Ile-Pro-Ala;

(SEQ ID NO: 1)
Ser-Ala-Leu-Leu-Arg-Ser-Ile-Pro-Ala;
and (SEQ ID NO: 28)
SALLRSIPAPAGASRLLLLTGEIDLP.
```

In one embodiment, the ADNF I polypeptide comprises up to about 20 or 40 amino acids at either or both of the N-terminus and the C-terminus of the active core site.

In another embodiment, the ADNF III polypeptide has the formula (R1)x-Asn-Ala-Pro-Val-Ser-Ile-Pro-Gln-(R2)y (SEQ ID NO:13), or an analogue thereof, in which
R1 is an amino acid sequence comprising from 1 to about 40 amino acids wherein each amino acid is independently selected from the group consisting of naturally occurring amino acids and amino acid analogs;
R2 is an amino acid sequence comprising from 1 to about 40 amino acids wherein each amino acid is independently selected from the group consisting of naturally occurring amino acids and amino acid analogs; and
x and y are independently selected and are equal to zero or one.

In another embodiment, the ADNF III polypeptide is a member selected from the group consisting of:

```
                                           (SEQ ID NO: 9)
Gly-Gly-Asn-Ala-Pro-Val-Ser-Ile-Pro-Gln;

(SEQ ID NO: 10)
Leu-Gly-Gly-Asn-Ala-Pro-Val-Ser-Ile-Pro-Gln-Gln-
Ser;

(SEQ ID NO: 11)
Leu-Gly-Leu-Gly-Gly-Asn-Ala-Pro-Val-Ser-Ile-Pro-
Gln-Gln-Ser;

(SEQ ID NO: 12)
Ser-Val-Arg-Leu-Gly-Leu-Gly-Gly-Asn-Ala-Pro-Val-
Ser-Ile-Pro-Gln-Gln-Ser;
and (SEQ ID NO: 2)
Asn-Ala-Pro-Val-Ser-Ile-Pro-Gln.
```

In another embodiment, the ADNF III polypeptide comprises up to about 20 amino acids at least one of the N-terminus and the C-terminus of the active core site.

In one embodiment, an ADNF I polypeptide of part (a) and an ADNF III polypeptide of part (b) are administered to the subject.

In one embodiment, the ADNF polypeptide is administered intranasally. In another embodiment, the ADNF polypeptide is administered orally. In another embodiment, the ADNF polypeptide is administered intravenously or subcutaneously.

In one aspect the invention provides the use of an ADNF polypeptide in the manufacture of a medicament for the treatment of peripheral neurotoxicity.

In one embodiment, the symptoms of said peripheral neurotoxicity are measured by motor dysfunction, muscle wasting, or a change selected from among a change in sense of smell, vision or hearing, deep tendon reflexes, vibratory sense, cutaneous sensation, gait and balance, muscle strength, orthostatic blood pressure, and chronic or intermittent pain.

In another embodiment, the peripheral neurotoxicity is a consequence of treatment with one or more chemical agents. In another embodiment, the peripheral neurotoxicity is a consequence of treatment with a chemical agent selected from among chemical agents for cancer, multiple sclerosis, gout, arthritis, Bechet's disease, psychiatric disorder, immunosuppression and infectious disease.

In another embodiment, one or more chemical agents is selected from among the vinca alkaloids (e.g., vincristine, vindesine, vinorelbine and vinblastine), platinum drugs (e.g., cisplatinum, carboplatinum), L-asparaginase and the taxanes (e.g., taxol, taxotere). In addition to anti-cancer agents, neurotoxicity may be caused by thalidomide, methotrexate, colchicine and anti-infective agents (including but not limited to nucleoside analogs such as lamivudine, zalcitabine, didanosine and stavudine).

In another embodiment, peripheral neurotoxicity is a consequence of a disease process. In another embodiment, the disease process selected from among diabetes, leprosy, Charcot-Marie-Tooth Disease, hereditary sensory and autonomic neuropathies (HSAN), Guillain-Barré syndrome, viral illnesses, (e.g., cytomegalovirus, Epstein-Barr virus, varicellazoster virus, and human immunodeficiency virus (HIV)), bacterial infection (including *Campylobacter jejuni* and Lyme disease), chronic alcoholism, botulism, poliomyelitis, uremia, chronic kidney failure, and atherosclerosis.

In another aspect, the present invention provides, the treatment of cancer or neoplasia comprising
  a) administering an anti-cancer agent; and
  b) administering, contemporaneously or sequentially with the anti-cancer agent of step a), an ADNF polypeptide in a pharmaceutically acceptable carrier.

In another aspect, the present invention provides a method of testing for response to a therapeutic agent for a neurodegenerative disease or peripheral neurotoxicity comprising the following steps,
  a) measuring olfaction capacity in a subject having a neurodegenerative disease or potential peripheral neurotoxicity;
  b) administering a therapeutic agent to the subject;
  c) measuring olfaction capacity in the subject subsequent to step b);
  d) comparing olfaction capacity from step a) and step c).

In another embodiment, the therapeutic agent is an ADNF polypeptide. In another embodiment, the neurodegenerative disease is Alzheimer's disease. In another embodiment, the subject has potential peripheral neurotoxicity associated with treatment by a chemotherapeutic agent.

In another aspect, the present invention provides a method of treatment of tauopathy in a subject comprising administering to a subject having or suspected of having a tauopathy, a therapeutically effective amount of an ADNF polypeptide.

BRIEF DESCRIPTION OF THE DRAWINGS

FIG. 3, for control rats, FIG. 4 for vincristine treated rats and FIG. 5 for vincristine and 25 microgram/kg NAP-treated rats. While the vincristine-treated rats did not show any initial interest in the new smell, a trend toward increased interest toward a new odor was observed in the control and the vincristine-NAP-treated rats.

DEFINITIONS

Figure 1:
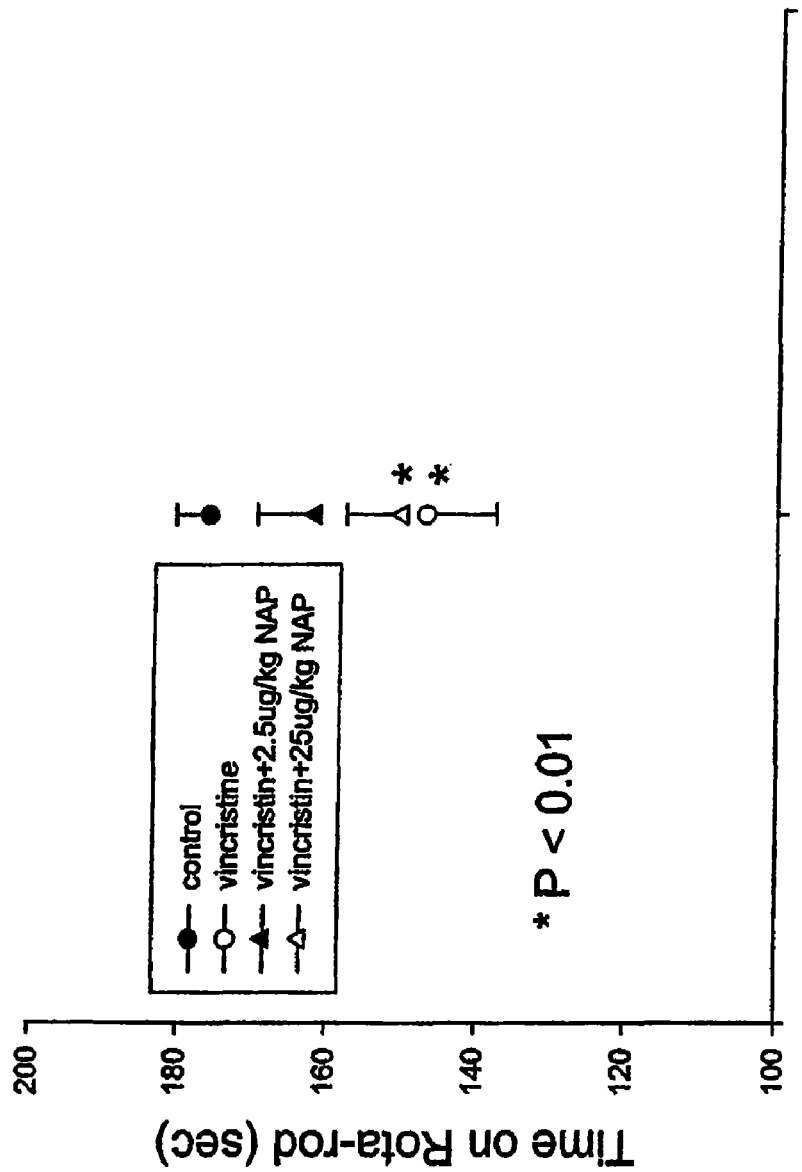
FIG. 1: Rota-rod tests were performed on rats receiving 0.175 mg/kg vincristine, and similar rats receiving vincristine plus subcutaneous NAP. Rota-rod test shows vincristine and NAP treated animals (n=10) perform better than vincristine treated alone (n=10). (**p<0.01).

The phrase "ADNF polypeptide" refers to one or more activity dependent neurotrophic factors (ADNF) that have an active core site comprising the amino acid sequence of SALLRSIPA (SEQ ID NO:1) (referred to as "SAL") or NAPVSIPQ (SEQ ID NO:2) (referred to as "NAP"), or conservatively modified variants thereof that have neurotrophic/ neuroprotective activity as measured with in vitro cortical neuron culture assays described by, e.g., Hill et al., Brain Res. 603:222-233 (1993); Brenneman & Gozes, J. Clin. Invest. 97:2299-2307 (1996), Gozes et al., Proc. Natl. Acad. Sci. USA 93, 427-432 (1996). An ADNF polypeptide can be an ADNF I polypeptide, an ADNF III polypeptide, their alleles, polymorphic variants, analogs, interspecies homolog, any subsequences thereof (e.g., SALLRSIPA (SEQ ID NO:1) or NAPVSIPQ (SEQ ID NO:2)) or lipophilic variants that exhibit neuroprotective/neurotrophic action on, e.g., neurons originating in the central nervous system either in vitro or in vivo. An "ADNF polypeptide" can also refer to a mixture of an ADNF I polypeptide and an ADNF III polypeptide.

The term "ADNF I" refers to an activity dependent neurotrophic factor polypeptide having a molecular weight of about 14,000 Daltons with a pI of 8.3±0.25. As described above, ADNF I polypeptides have an active site comprising an amino acid sequence of Ser-Ala-Leu-Leu-Arg-Ser-Ile-Pro-Ala (SEQ ID NO:1) (also referred to as "SALLRSIPA" or "SAL" or "ADNF-9"). See Brenneman & Gozes, J. Clin. Invest. 97:2299-2307 (1996), Glazner et al., Anat. Embryol. ((Berl). 200:65-71 (1999), Brenneman et al., J. Pharm. Exp. Ther., 285:619-27 (1998), Gozes & Brenneman, J. Mol. Neurosci. 7:235-244 (1996), and Gozes et al., Dev. Brain Res. 99:167-175 (1997). Unless indicated as otherwise, "SAL" refers to a peptide having an amino acid sequence of Ser-Ala-Leu-Leu-Arg-Ser-Ile-Pro-Ala (SEQ ID NO:1), not a peptide having an amino acid sequence of Ser-Ala-Leu. A full length amino acid sequence of ADNF I can be found in WO 96/11948.

The phrase "ADNF III polypeptide" or "ADNF III" also called activity-dependent neuroprotective protein (ADNP) refers to one or more activity dependent neurotrophic factors (ADNF) that have an active core site comprising the amino acid sequence of NAPVSIPQ (SEQ ID NO:2) (referred to as "NAP"), or conservatively modified variants thereof that have neurotrophic/neuroprotective activity as measured with in vitro cortical neuron culture assays described by, e.g., Hill et al., Brain Res. 603, 222-233 (1993); Gozes et al., Proc. Natl. Acad. Sci. USA 93, 427-432 (1996). An ADNF polypeptide can be an ADNF III polypeptide, allelelic or polymorphic variant, analog, interspecies homolog, or any subsequences thereof (e.g., NAPVSIPQ; SEQ ID NO:2) that exhibit neuroprotective/neurotrophic action on, e.g., neurons originating in the central nervous system either in vitro or in vivo. ADNF III polypeptides can range from about eight amino acids and can have, e.g., between 8-20, 8-50, 10-100 or about 1000 or more amino acids.

Full length human ADNF III has a predicted molecular weight of 123,562.8 Da (>1000 amino acid residues) and a pI of about 6.97. As described above, ADNF III polypeptides have an active site comprising an amino acid sequence of Asn-Ala-Pro-Val-Ser-Ile-Pro-Gln (SEQ ID NO:2) (also referred to as "NAPVSIPQ" or "NAP"). See Zamostiano et al., J. Biol. Chem. 276:708-714 (2001) and Bassan et al., J. Neurochem. 72:1283-1293 (1999). Unless indicated as otherwise, "NAP" refers to a peptide having an amino acid sequence of Asn-Ala-Pro-Val-Ser-Ile-Pro-Gln (SEQ ID NO:2), not a peptide having an amino acid sequence of Asn-Ala-Pro. Full-length amino acid and nucleic acid sequences of ADNF III can be found in WO 98/35042, WO 00/27875, U.S. Pat. No. 6,613,740. The Accession number for the human sequence is NP_852107, see also Zamostiano et al., infra.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO 01/12654, incorporated herein by reference, which may improve oral availability and other drug like characteristics of the compound. In such embodiments, one or more, and potentially all of the amino acids of NAP or the ADNF polypeptide will have D-chirality. The therapeutic use of peptides can be enhanced by using D-amino acids to provide longer half life and duration of action. However, many receptors exhibit a strong preference for L-amino acids, but examples of D-peptides have been reported that have equivalent activity to the naturally occurring L-peptides, for example, pore-forming antibiotic peptides, beta amyloid peptide (no change in toxicity), and endogenous ligands for the CXCR4 receptor. In this regard, NAP and ADNF polypeptides also retain activity in the D-amino acid form (Brenneman et al., *J. Pharmacol. Exp. Ther.* 309(3):1190-7 (2004), infra).

Amino acids may be referred to by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W). (see, e.g., Creighton, *Proteins* (1984)).

One of skill in the art will appreciate that many conservative variations of the nucleic acid and polypeptide sequences provided herein yield functionally identical products. For example, due to the degeneracy of the genetic code, "silent substitutions" (i.e., substitutions of a nucleic acid sequence that do not result in an alteration in an encoded polypeptide) are an implied feature of every nucleic acid sequence that encodes an amino acid. Similarly, "conservative amino acid substitutions," in one or a few amino acids in an amino acid sequence are substituted with different amino acids with highly similar properties (see the definitions section, supra), are also readily identified as being highly similar to a disclosed amino acid sequence, or to a disclosed nucleic acid sequence that encodes an amino acid. Such conservatively substituted variations of each explicitly listed nucleic acid and amino acid sequences are a feature of the present invention.

The term "subject" refers to any mammal, in particular human, at any stage of life.

The term "contacting" is used herein interchangeably with the following: combined with, added to, mixed with, passed over, incubated with, flowed over, etc. Moreover, the ADNF III polypeptides or nucleic acids encoding them of the present invention can be "administered" by any conventional method such as, for example, parenteral, oral, topical, and inhalation routes. In some embodiments, parenteral and nasal inhalation routes are employed.

"Neurotoxicity" as used herein is defined as adverse effects on the structure or functioning of the cells of the nervous system that result from exposure to chemical substances or to disease processes. Among other things, neurotoxicants can cause morphological changes that lead to generalized damage to nerve cells (neuronopathy), injury to axons (axonopathy), or destruction of the myelin sheath (myelinopathy). It is well established that exposure to certain chemotherapeutic agents, agricultural and industrial chemicals can damage the nervous system, resulting in neurological and behavioral dysfunction. Symptoms of neurotoxicity include muscle weakness, loss of sensation and motor control, tremors, alterations in cognition, and impaired functioning of the autonomic nervous system. Neurotoxicological assessments use a battery of functional and observational tests. Neurotoxicity in humans is most commonly measured by neurological tests that assess cognitive, sensory, and motor function.

"Peripheral neurotoxicity" refers to neurotoxicity of the peripheral nervous system (PNS). The PNS includes all the nerves not in the brain or spinal cord, and includes the dorsal root ganglia (DRG). These nerves carry sensory information and motor impulses. Damage to the nerve fibers of the PNS can disrupt communication between the CNS and the rest of the body. Peripheral neurotoxicity is also sometimes referred to in the literature as peripheral neuropathy, and can include hundreds of identifiable conditions, as further described below. "Peripheral neuropathy" encompasses a wide range of conditions in which the nerves outside of the brain and spinal cord have been damaged, and may include crush injury and section.

"Central nervous system" or "CNS" means the brain and spinal cord.

The terms "polypeptide," "peptide" and "protein" are used interchangeably herein to refer to a polymer of amino acid residues. Generally, a peptide refers to a short polypeptide. The terms apply to amino acid polymers in which one or more amino acid residue is an analog or mimetic of a corresponding naturally occurring amino acid, as well as to naturally occurring amino acid polymers.

As used herein 'treatment' includes preventative treatment or prophylaxis, such as treatment for prevention of disease progression or onset of further symptoms, or for avoidance or reduction of side-effects or symptoms of a disease.

As used herein, 'disease' includes an incipient condition or disorder or symptoms of a disease, incipient condition or disorder.

The terms "isolated," "purified" or "biologically pure" refer to material that is substantially or essentially free from components that normally accompany it as found in its native state.

"An amount sufficient" or "an effective amount" or a "therapeutically effective amount" is that amount of an ADNF polypeptide that exhibits the activity of interest or which provides either a subjective relief of a symptom(s) or an objectively identifiable improvement as noted by the clinician or other qualified observer. In therapeutic applications, the ADNF polypeptides of the invention are administered to a patient in an amount sufficient to reduce or eliminate symptoms of the disease. An amount adequate to accomplish this is defined as the "therapeutically effective dose." The dosing range varies with the ADNF polypeptide used, the route of administration and the potency of the particular ADNF polypeptide, as further set out below, and as described in patents CA Patent 2202496, U.S. Pat. No. 6,174,862 and U.S. Pat. No. 6,613,740.

"Inhibitors," "activators," and "modulators" of expression or of activity are used to refer to inhibitory, activating, or modulating molecules, respectively, identified using in vitro and in vivo assays for expression or activity, e.g., ligands, agonists, antagonists, and their homologs and mimetics. The term "modulator" includes inhibitors and activators. Inhibitors are agents that, e.g., inhibit expression of a polypeptide or polynucleotide of the invention or bind to, partially or totally block stimulation or enzymatic activity, decrease, prevent, delay activation, inactivate, desensitize, or down regulate the activity of a polypeptide or polynucleotide of the invention, e.g., antagonists. Activators are agents that, e.g., induce or activate the expression of a polypeptide or polynucleotide of the invention or bind to, stimulate, increase, open, activate, facilitate, enhance activation or enzymatic activity, sensitize or up regulate the activity of a polypeptide or polynucleotide of the invention, e.g., agonists. Modulators include naturally occurring and synthetic ligands, antagonists, agonists, small chemical molecules and the like. Assays to identify inhibitors and activators include, e.g., applying putative modulator compounds to cells, in the presence or absence of a polypeptide or polynucleotide of the invention and then determining the functional effects on a polypeptide or polynucleotide of the invention activity. Samples or assays comprising a polypeptide or polynucleotide of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a polypeptide or polynucleotide of the invention relative to the control is about 80%, optionally 50% or 25-1%. Activation is achieved when the activity value of a polypeptide or polynucleotide of the invention relative to the control is 110%, optionally 150%, optionally 200-500%, or 1000-3000% higher.

DETAILED DESCRIPTION OF THE INVENTION

This invention discloses the surprising finding that an ADNF polypeptide that was shown previously to be neuroprotective of the CNS and to provide cognitive enhancement can alternatively be used in the treatment of peripheral neurotoxicity induced by chemical agents or disease processes. The invention is supported by the findings set out in the Examples that in vivo administration of NAP peptide significantly reduces peripheral neurotoxicity induced by chemical agents.

ADNF Polypeptides: Composition and Synthesis

In one embodiment, the ADNF polypeptides of the present invention comprise the following amino acid sequence: $(R^1)_x$-Asn-Ala-Pro-Val-Ser-Ile-Pro-Gln-$(R^2)_y$ (SEQ ID NO:13) and conservatively modified variations thereof. In this designation, $R^1$ denotes the orientation of the amino terminal ($NH_2$ or N-terminal) end and $R^2$ represents the orientation of the carboxyl terminal (COOH or C-terminal) end.

In the above formula, $R^1$ is an amino acid sequence comprising from 1 to about 40 amino acids, wherein each amino acid is independently selected from the group consisting of naturally occurring amino acids and amino acid analogs. The term "independently selected" is used herein to indicate that the amino acids making up the amino acid sequence $R^1$ may be identical or different (e.g., all of the amino acids in the amino acid sequence may be threonine, etc.). Moreover, as previously explained, the amino acids making up the amino acid sequence $R^1$ may be either naturally occurring amino acids, or known analogues of natural amino acids that functions in a manner similar to the naturally occurring amino acids (i.e., amino acid mimetics and analogs). Suitable amino acids that can be used to form the amino acid sequence $R^1$ include, but are not limited to, those listed in Table I, infra. The indexes "x" and "y" are independently selected and can be equal to one or zero.

As with $R^1$, $R^2$, in the above formula, is an amino acid sequence comprising from 1 to about 40 amino acids, wherein each amino acid is independently selected from the group consisting of naturally occurring amino acids and amino acid analogs. Moreover, as with $R^1$, the amino acids making up the amino acid sequence $R^2$ may be identical or different, and may be either naturally occurring amino acids, or known analogues of natural amino acids that functions in a manner similar to the naturally occurring amino acids (i.e., amino acid mimetics and analogs). Suitable amino acids that can be used to form $R^2$ include, but are not limited to, those listed in Table I, infra.

As used herein, "NAP" or "NAP peptide" refers to the formula above where x and y both equal 0. "NAP related peptide" refers to any of the other variants of NAP which are described the formula.

$R^1$ and $R^2$ are independently selected. If $R^1$ $R^2$ are the same, they are identical in terms of both chain length and amino acid composition. For example, both $R^1$ and $R^2$ may be Val-Leu-Gly-Gly-Gly (SEQ ID NO:14). If $R^1$ and $R^2$ are different, they can differ from one another in terms of chain length and/or amino acid composition and/or order of amino acids in the amino acids sequences. For example, R¹ may be Val-Leu-Gly-Gly-Gly (SEQ ID NO:14), whereas R² may be Val-Leu-Gly-Gly (SEQ ID NO:15). Alternatively, R¹ may be Val-Leu-Gly-Gly-Gly (SEQ ID NO:14), whereas R² may be Val-Leu-Gly-Gly-Val (SEQ ID NO:16). Alternatives, R¹ may be Val-Leu-Gly-Gly-Gly (SEQ ID NO:14), whereas R² may be Gly-Val-Leu-Gly-Gly (SEQ ID NO:17).

Within the scope of the above formula, certain NAP and NAP related polypeptides are preferred, namely those in which x and y are both zero (i.e. NAP). Equally preferred are NAP and NAP related polypeptides in which x is one; R¹ Gly-Gly; and y is zero. Also equally preferred are NAP and NAP related polypeptides in which is one; R¹ is Leu-Gly-Gly; y is one; and R² is -Gln-Ser. Also equally preferred are NAP and NAP related polypeptides in which x is one; R¹ is Leu-Gly-Leu-Gly-Gly- (SEQ ID NO:18); y is one; and R² is -Gln-Ser. Also equally preferred are NAP and NAP related polypeptides in which x is one; R¹ is Ser-Val-Arg-Leu-Gly-Leu-Gly-Gly- (SEQ ID NO:19); y is one; and R² is -Gln-Ser. Additional amino acids can be added to both the N-terminus and the C-terminus of the active peptide without loss of biological activity.

In another aspect, the present invention provides pharmaceutical compositions comprising one of the previously described NAP and NAP related polypeptides in an amount sufficient to exhibit desired therapeutic activity, in a pharmaceutically acceptable diluent, carrier or excipient. In one embodiment, the NAP or NAP related peptide has an amino acid sequence selected from the group consisting of SEQ ID NO:2, and 9-12, and conservatively modified variations thereof.

In another embodiment, the ADNF polypeptide comprises the following amino acid sequence: $(R^1)_x$-Ser-Ala-Leu-Leu-Arg-Ser-Ile-Pro-Ala-$(R^2)_y$ (SEQ ID NO:27) and conservatively modified variations thereof. In this designation, R¹ denotes the orientation of the amino terminal (NH₂ or N-terminal) end and R² represents the orientation of the carboxyl terminal (COOH or C-terminal) end.

In the above formula, R¹ is an amino acid sequence comprising from 1 to about 40 amino acids, wherein each amino acid is independently selected from the group consisting of naturally occurring amino acids and amino acid analogs. The term "independently selected" is used herein to indicate that the amino acids making up the amino acid sequence R¹ may be identical or different (e.g., all of the amino acids in the amino acid sequence may be threonine, etc.). Moreover, as previously explained, the amino acids making up the amino acid sequence R¹ may be either naturally occurring amino acids, or known analogues of natural amino acids that functions in a manner similar to the naturally occurring amino acids (i.e., amino acid mimetics and analogs). Suitable amino acids that can be used to form the amino acid sequence R¹ include, but are not limited to, those listed in Table I, infra. The indexes "x" and "y" are independently selected and can be equal to one or zero.

As with R¹, R², in the above formula, is an amino acid sequence comprising from 1 to about 40 amino acids, wherein each amino acid is independently selected from the group consisting of naturally occurring amino acids and amino acid analogs. Moreover, as with R¹, the amino acids making up the amino acid sequence R² may be identical or different, and may be either naturally occurring amino acids, or known analogues of natural amino acids that functions in a manner similar to the naturally occurring amino acids (i.e., amino acid mimetics and analogs). Suitable amino acids that can be used to form R² include, but are not limited to, those listed in Table I, infra.

As used herein, "SAL" or "SAL peptide" refers to the formula above where x and y both equal 0. "SAL related peptide" refers to any of the other variants of SAL which are described the formula.

R¹ and R² are independently selected. If R¹ R² are the same, they are identical in terms of both chain length and amino acid composition. Additional amino acids can be added to both the N-terminus and the C-terminus of the active peptide without loss of biological activity.

In another aspect, the present invention provides pharmaceutical compositions comprising one of the previously described SAL and SAL-related polypeptides in an amount sufficient to desired therapeutic activity, in a pharmaceutically acceptable diluent, carrier or excipient. In one embodiment, the SAL or SAL related peptide has an amino acid sequence selected from the group consisting of SEQ ID NO:1 and 3-8, and conservatively modified variations thereof. In a further embodiment, the SAL related peptide comprises SALLRSIPAPAGASRLLLLTGEIDLP (SEQ ID NO:21). The sequence SALLRSIPAPAGASRLLLLTGEIDLP (SEQ ID NO:21) is also known as Colivelin and is a combination of the SAL active site and a derivative of the Humanin protein named AGA-(C8R)HNG17. Colivelin is described in Chiba et al., *J. Neurosci.* 25:10252-10261 (2005), which is herein incorporated by reference for all purposes.

It will be readily apparent to those of ordinary skill in the art that preferred ADNF polypeptides can readily be selected for peripheral neuroprotective activity by employing suitable assays and animal models known to those skilled in the art, some of which are disclosed herein.

In addition, one of skill in the art will recognize that a variety of chemical modifications can be made to the peptides without diminishing their biological activity. In addition to replacement of specific amino acids with other amino acids, there may also be a wide range of modifications to specific amino acids, and conjugates with a wide variety of polymers, proteins, carbohydrates or other organic moieties.

The peptides of the invention may be prepared via a wide variety of well-known techniques. Peptides of relatively short size are typically synthesized on a solid support or in solution in accordance with conventional techniques (see, e.g., Merrifield, *Am. Chem. Soc.* 85:2149-2154 (1963)). Various automatic synthesizers and sequencers are commercially available and can be used in accordance with known protocols (see, e.g., Stewart & Young, *Solid Phase Peptide Synthesis* (2nd ed. 1984)). Solid phase synthesis in which the C-terminal amino acid of the sequence is attached to an insoluble support followed by sequential addition of the remaining amino acids in the sequence is the preferred method for the chemical synthesis of the peptides of this invention. Techniques for solid phase synthesis are described by Barany & Merrifield, *Solid-Phase Peptide Synthesis*; pp. 3-284 in *The Peptides: Analysis, Synthesis, Biology.* Vol. 2: *Special Methods in Peptide Synthesis*, Part A.; Merrifield et al 1963; Stewart et al. 1984). NAP and related peptides are synthesized using standard Fmoc protocols (Wellings & Atherton, *Methods Enzymol.* 289:44-67 (1997)).

Other synthetic methods for peptides include liquid phase synthesis (e.g. Fischer and Zheleva *J Pept Sci.* 8(9):529-42 (2002).

In addition to the foregoing techniques, the ADNF peptides, in particular the full length proteins ADNF I and ADNF III for use in the invention may be prepared by recombinant DNA methodology. Generally, this involves creating a nucleic acid sequence that encodes the protein, placing the nucleic acid in an expression cassette under the control of a particular promoter, and expressing the protein in a host cell.

Recombinantly engineered cells known to those of skill in the art include, but are not limited to, bacteria, yeast, plant, filamentous fungi, insect (especially employing baculoviral vectors) and mammalian cells.

Use of ADNF Polypeptides for Treating Peripheral Neurotoxicity

Peripheral neurotoxicity may be identified and diagnosed in a subject by a variety of techniques. Typically it may be measured by motor dysfunction, muscle wasting, or a change in sense of smell, vision or hearing, or changes in deep tendon reflexes, vibratory sense, cutaneous sensation, gait and balance, muscle strength, orthostatic blood pressure, and chronic or intermittent pain. In humans these symptoms are also sometimes demonstrative of toxic effects in both the PNS and the CNS. Ultimately, there are hundreds of possible peripheral neuropathies that may result from neurotoxicity. Reflecting the scope of PNS activity, symptoms may involve sensory, motor, or autonomic functions. They can be classified according to the type of affected nerves and how long symptoms have been developing.

Peripheral neurotoxicity can be induced by chemotherapeutic agents (anti-cancer, anti-microbial and the like) and by disease processes. These two different areas are discussed separately below.

Regarding chemotherapeutic agents, it is well known that patients exposed to agents such as Vinca alkaloids, suramin, taxanes, and cisplatin can develop peripheral neurotoxicity. Neurological observations published in recent years indicate that administration of taxanes and cisplatin in patients affected by neoplasm induces nerve deficits in a dose- and time-dependent manner. (Bedikian A. Y., et al. 1995. *J. Clin. Oncol.*, 13: 2895-2899). Moreover, when platinum compounds and taxanes are used in combination, the patients develop more severe peripheral neuropathies. The pathophysiology of chemotherapeutic agent-induced neuropathy is still not clear, although a variety of studies have shown that taxanes interfere with axonal transport, causing axonal distal sensory-motor lesions, whereas platinum compounds induce sensory neuropathy acting mainly on the neuronal cell bodies of the spinal ganglion. Pathological and electrophysiological studies have also indicated that neurons of the dorsal root ganglion are selectively damaged after cisplatin treatment. It has been reported that the development of this peripheral neurotoxicity can induce clinicians to interrupt therapy to prevent more severe neurological deficits (Amato A. A., Collins M. P. *Semin. Neurol.*, 18: 125-142, 1998.). Because of the neurotoxic effects, much effort has been devoted to the identification of potential neuroprotective agents. It is reasonable, therefore, to hypothesize that ADNF polypeptides, which can prevent neurotoxicity and/or promote peripheral innervation after chemotherapy, will be clinically useful. Those skilled in the art are familiar with chemotherapeutic agents that may cause peripheral neurotoxicities. In general such chemotherapeutic agents are used in the treatment of cancer, multiple sclerosis, gout, arthritis, Bechet's disease, psychiatric disorders, familial Mediterranean fever, amyloidosis, immunosuppression and infectious disease. A representative list includes vinca alkaloids (vincristine, vindesine, vinorelbine and vinblastine), platinum drugs (cisplatinum, carboplatinum), L-asparaginase and the taxanes (taxol, taxotere). In addition to anti-cancer agents, neurotoxicity may be cause by thalidomide, methotrexate, colchicine and anti-infective agents (including but not limited to nucleoside analogs such as lamivudine, zalcitabine, didanosine and stavudine).

The method of the invention recognizes that administration of a therapeutically effective amount of an ADNF polypeptide is useful to treat or prevent peripheral neurotoxicity in a subject receiving a chemotherapeutic agent, such as those described above. Relative to the administration of the chemotherapeutic agent, the administration of the ADNF polypeptide can occur before, at the same time, subsequent to or on an irregular basis. Those skilled in the art are able to identify a suitable temporal relationship between the agents which is designed to establish peripheral neuroprotection before the consequences of the neurotoxicity develop. Treatment may continue until chemotherapeutic agent is discontinued, or until the neurotoxicity resulting from the agent is resolved and not expected to worsen.

When administered non-contemporaneously (e.g. sequentially) with the chemotherapeutic agent, the ADNF polypeptide will typically be formulated separately from the agent. When administered contemporaneously, it may be advantageous to provide the ADNF polypeptide in a dosage form in combination with the agent. Thus the invention recognizes a formulation of a chemotherapeutic agent and an ADNF polypeptide, wherein the dose of the ADNF polypeptide is effective to reduce or eliminate the peripheral neurotoxicity associated with the chemotherapeutic agent. Those skilled in the art are able to select a proper dose of ADNF polypeptide based this disclosure and on the anticipated neurotoxic effects of the selected chemotherapeutic agent.

As mentioned previously, certain disease processes can also result in peripheral neurotoxicity. For example, the diabetes/peripheral neuropathy link has been well established. A typical pattern of diabetes-associated neuropathic symptoms includes sensory effects that first begin in the feet. The associated pain or pins-and-needles, burning, crawling, or prickling sensations form a typical "stocking" distribution in the feet and lower legs.

Other diseases that may result in peripheral neurotoxicity include inherited or acquired disorders, including infectious diseases. Such diseases include leprosy, Charcot-Marie-Tooth Disease, Inherited neurological disorders such as the hereditary sensory and autonomic neuropathies (HSAN), Guillain-Barré syndrome which may arise from complications associated with viral illnesses, such as cytomegalovirus, Epstein-Barr virus, and human immunodeficiency virus (HIV), or bacterial infection, including *Campylobacter jejuni* and Lyme disease. Other well-known causes of peripheral neuropathies include chronic alcoholism, infection varicella-zoster virus, botulism, and poliomyelitis. Peripheral neuropathy may develop as a primary symptom, or it may be less significant. Uremia, or chronic kidney failure, carries a 10-90% risk of eventually developing neuropathy, and there may be an association between liver failure and peripheral neuropathy. Accumulation of lipids inside blood vessels (atherosclerosis) can choke-off blood supply to certain peripheral nerves.

As recognized in the case of chemotherapeutic agents, use of ADNF polypeptides to treat or prevent neurotoxicity from disease processes requires administration of a therapeutically effective amount of an ADNF polypeptide sufficient to treat or prevent peripheral neurotoxicity in a subject suffering from such disease. In this case, relative to the onset of the peripheral neurotoxicity, the administration of the ADNF polypeptide can occur before, at the same time, subsequent to or on an irregular basis. Those skilled in the art are able to identify a suitable temporal relationship between the agents which is designed to establish peripheral neuroprotection before the consequences of the disease induced neurotoxicity develop. Treatment may continue until the underlying disease resolves, or until the neurotoxicity resulting from the disease is resolved and not expected to worsen. In some cases, administration of ADNF polypeptides may be chronic.

Because the disease processes of concern to this invention are often treated with other therapeutic agents, the invention recognizes that it may be advantageous to provide the ADNF polypeptide in a dosage form in combination with such an agent. Thus the invention recognizes a formulation of a therapeutic agent and an ADNF polypeptide, wherein the dose of the ADNF polypeptide is effective to reduce or eliminate the peripheral neurotoxicity associated with the chemotherapeutic agent. Those skilled in the art are able to select a proper dose of ADNF polypeptide based this disclosure and on the anticipated neurotoxic effects of the selected therapeutic agent.

Use of ADNF Polypeptides to Treat Tauopathy and Related Diseases

Tauopathy means the accumulation of microtubule-associated protein tau in the neuronal and glial cytoplasm. This terminology is relatively new, but it relates to neurodegenerative diseases evidencing widespread accumulation of tau epitopes both in neurons and glia, sometimes without deposition of amyloid beta protein. Tauopathy is now considered to be one of the primary causes of neuronal degeneration, with about one third of the very elderly presenting with deposition of abnormally phosphorylated tau proteins with relative paucity of amyloid beta protein (Abeta). In the course of neurofibrillary tangle formation (including tau aggregates), the major proteinaceous components of these lesions undergo post-translational modifications. In the case of tau, these include phosphorylation of mainly serine and threonine, but also tyrosine residues. In addition, tau is subject to ubiquitination, nitration, truncation, prolyl isomerization, association with heparan sulfate proteoglycan, glycosylation, glycation and modification by advanced glycation end-products (AGEs). Human tauopathies include Alzheimer's disease and frontotemporal dementia with parkinsonism linked to chromosome 17 (Chen et al. *Curr Drug Targets.* 5(6):503-15 (2004)). Furthermore, recent studies have shown that as a consequence of chemotherapy there was an increase in cerebrospinal fluid tau, which is a marker of neurodegeneration (Van Gool et al. *Leukemia.* 14:2076-84 (2000); Lee et al., *Biochem. Biophys Acta.* 1739: 251-9 (2005))

The instant invention relates to a method of treatment of tauopathy in a subject comprising administering to the subject a therapeutically effective amount of an ADNF polypeptide. Treatment of tauopathy with the NAP peptide is a specific embodiment of this invention.

The inventors have recognized, based on the instant disclosure, that ADNF polypeptides such as NAP effectively prevent neurotoxic damage by the vinca alkaloid vincristine (see Examples), and without wishing to be bound to any particular theory or mechanism of action, that this effect of NAP can be combined with the teachings of PCT publication WO 2004/080957 (Gozes et al.) and Divinski et al. *J Biol Chem.* 279 (27):28531-8. (2004) that demonstrate that NAP interacts with tubulin to enhance microtubule formation and stabilize microtubular structure in glial and neural cells, to establish for the first time that NAP is useful for the treatment of tauopathy. Other peptides of the ADNF family including ADNF-9 (or SAL) and all D-amino acids SAL (termed D-SAL, Brenneman et al. (2004), infra) as well as full length ADNP (ADNFIII) interact with tubulin. (Furman et al., *Neuron Glia Biology* 1:193-9 (2004).

It is well recognized that tau performs an important function of stabilizing and maintaining the microtubular network, that in turn is important for axonal transport in neurons. The formation of the pathological neurofibrillary tangles which results from the hyperphosphorylation of tau, leads to microtubule breakdown and impaired axonal transport (Ishihara et al. *Neuron* 24:751-62 (1999); Lee et al., *Annu Rev Neurosci.* 24:1121-59 (2001); Morfini et al. *Neuromolecular Med.* 2:89-99 (2002); Gozes. *J Mol Neurosci.* 19(3):337-8 (2002)). Divinski et al. *J Biol Chem.* 279(27):28531-8. (2004) have demonstrated that exposure to zinc toxicity resulted in microtubule breakdown in astrocytes and neurons and that NAP protects these cells from this toxicity by promoting the reorganization of the microtubular network. In the same experiments, tubulin was identified as a NAP binding molecule. Furthermore, in the presence of NAP, there is an increase in the ratio of non-phosphorylated tau to phosphorylated tau (Gozes & Divinski, *Journal of Alzheimer's Disease* 6(6 Suppl.):S37-41 (2004)) and increased neurite outgrowth, a process that is dependent on slow axoplasmic transport (Lagreze et al., *Invest Opthalmol Vis Sci.* 46:933-8 (2005); Gozes. *Neurochem Int.* 4:101-20 (1982); Smith-Swintosky et al. *J Mol Neurosci.* 25:225-38 (2005). Therefore, it is possible that NAP functions to promote the assembly and stability of the microtubular network either directly by binding to tubulin or indirectly through changes in the levels of the different forms of tau. The promotion of proper microtubule assembly is also important in the case of vicristine treatment, as vincristine and related compounds facilitate the tubulin spiral filaments and aggregated spiral formation (Verdier-Pinard et al. *Biochem Pharmacol.* 58(6):959-71 (1999)) Any other tubulin binding and modifying agents including, but not limited to vinca alkaloids (vincristine, vindesine, vinorelbine and vinblastine), the taxanes (taxol, taxotere), nocodazole and colchicines will affect axoplasmic transport which can in turn be protected by the specific neuroprotective effect of NAP treatment (Gozes et al. *J Mol Neurosci.* 20(3):315-22, (2003)).

Use of Olfaction Testing to Measure Effectiveness of Neurological Therapeutics, such as ADNF Polypeptides.

Olfaction disabilities, including hyposmia (reduction in ability to taste and smell) or anosmia (total loss of ability to taste and smell), are associated with neurodegenerative disease (such as Alzheimer's disease, multiple sclerosis, Huntington disease, amyotrophic lateral sclerosis, Parkinson's disease and others) and peripheral neurotoxicity induced by chemotherapeutic agents and by disease processes. In all these cases, olfaction disabilities are generally progressive.

The present invention provides a method to identify whether a subject having a neurodegenerative disease or peripheral neurotoxicity is responding to therapeutic agents administered to treat the disease by measuring olfaction in the subject. A response to therapy is indicated either by an improvement in olfaction capacity or quality of the subject after treatment with a therapeutic agent, or at least a reduction, after such treatment, in the degree of hyposmia or the progress of hyposmia to anosmia that would be expected in subjects with untreated disease.

While the method can be used to test response to any therapeutic agent for the treatment of the neurodegenerative disease or the peripheral neurotoxicity, in particular, this invention provides a method to identify a response to therapy with ADNF polypeptide.

The method involves testing for response to a therapeutic agent for a neurodegenerative disease comprising the following steps: a) measuring olfaction capacity in a subject having a neurodegenerative disease or potential peripheral neurotoxicity; b) administering a therapeutic agent to the subject; c) measuring olfaction capacity in the subject subsequent to step b); and d) comparing olfaction capacity from step a) and step c).

Based on the results of the comparison of step d), the subject and care-giver can determine whether there is either an improvement in olfaction capacity or quality of the subject after treatment with a therapeutic agent, or at least a reduction, after such treatment, in the degree of hyposmia or the progress of hyposmia to anosmia that would be expected in subjects with untreated disease, thus indicating a response to the therapeutic agent, or not. Patients and care-givers can then go on to decide whether treatment with the therapeutic agent should continue or be halted.

This method provides many advantages for assessing a response to a therapeutic agent, in particular because olfaction is one of the first senses to be lost or diminished as a result of a neurodegenerative disease or the onset of peripheral neurotoxicity.

Pharmaceutical Administration

ADNF polypeptides of the invention are generally administered in a pharmaceutical formulation. Suitable formulations for use in the present invention are found in Remington's *Pharmaceutical Sciences* (17th ed. 1985). In addition, for a brief review of methods for drug delivery, see Langer, *Science* 249:1527-1533 (1990).

As such, the present invention provides for therapeutic compositions or medicaments comprising one or more of the ADNF polypeptides described herein in combination with a pharmaceutically acceptable excipient, wherein the amount of the ADNF polypeptide is sufficient to provide a therapeutic effect.

The ADNF polypeptides of the present invention are embodied in pharmaceutical compositions intended for administration by any effective means, including parenteral, topical, nasal, oral, pulmonary (e.g. by inhalation) or local administration. Preferably, the pharmaceutical compositions are administered parenterally, e.g., intravenously, subcutaneously, intradermally, intramuscularly, or intranasally.

Thus, the invention provides compositions for parenteral administration that comprise a solution of ADNF polypeptide, as described above, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride potassium chloride, calcium chloride, sorbitan monolaurate, triethanolamine oleate, etc.

For solid compositions, conventional nontoxic solid carriers may be used that include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol administration, the ADNF polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery. An example includes a solution in which each milliliter included 7.5 mg NaCl, 1.7 mg citric acid monohydrate, 3 mg disodium phosphate dihydrate and 0.2 mg benzalkonium chloride solution (50%) (Gozes et al., *J Mol Neurosci.* 19(1-2):167-70 (2002)). The ADNF polypeptides of the invention can therefore be used in the manufacture of a medicament for the treatment or prevention of peripheral neurotoxicity. The medicament can comprise any of the pharmaceutical formulations contemplated herein, with any amount of active ingredient (e.g. ADNF polypeptide) contemplated herein.

In therapeutic applications, the ADNF polypeptides of the invention are administered to a patient in an amount sufficient to reduce or eliminate symptoms of peripheral neurotoxicity. An amount adequate to accomplish this is defined as "therapeutically effective dose." Amounts effective for this use will depend on, for example, the particular NAP or ADNF polypeptide employed, the type of disease or disorder to be prevented, the manner of administration, the weight and general state of health of the patient, and the judgment of the prescribing physician.

For example, an amount of polypeptide falling within the range of a 100 ng to 10 mg dose given intranasally once a day (e.g., in the evening) would be a therapeutically effective amount. Alternatively, dosages may be outside of this range, or on a different schedule. For example, dosages may range from 0.0001 mg/kg to 1000 mg/kg, and will preferably be about 0.001 mg/kg, 0.1 mg/kg, 1 mg/kg, 5 mg/kg, 50 mg/kg or 500 mg/kg per dose. Doses may be administered hourly, every 4, 6 or 12 hours, with meals, daily, every 2, 3, 4, 5, 6, or 7 days, weekly, every 2, 3, 4 weeks, monthly or every 2, 3 or 4 months, or any combination thereof. The duration of dosing may be single (acute) dosing, or over the course of days, weeks, months, or years, depending on the condition to be treated. Those skilled in the art can determine the suitable dosage, and may rely on preliminary data reported in Gozes et al., 2000, Gozes et al., 2002), Bassan et al. 1999; Zemlyak et al., *Regul. Pept.* 96:39-43 (2000); Brenneman et al., *Biochem. Soc. Trans.* 28: 452-455 (2000); *Erratum Biochem Soc. Trans.* 28:983; Wilkemeyer et al. *Proc. Natl. Acad. Sci. USA* 100: 8543-8548 (2003)). Suitable dose ranges are described in the examples provided herein, as well as in WO 9611948.

It must be noted that as used herein and in the appended claims, the singular forms "a", "and", and "the" include plural referents unless the context clearly dictates otherwise. Thus, for example, reference to "a cell" includes a plurality of such cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. Citations are incorporated herein by reference.

EXAMPLES

Example 1

Intranasal Administration of NAP Decreases Peripheral Neurotoxicity Induced by Vinca Alkaloids in Rats

The present study was designed to evaluate if NAP treatment successfully reduced peripheral neurotoxicity induced by the vinca alkaloid vincristine in rats.

Methods

Rats (200-300 g), divided into 4 groups of 10, were injected with vincristine sulfate dissolved in saline. Stock concentration was 2 mg/ml, pH 4.5-5.2. Aliquots of the drug were diluted daily in saline to concentrations of 0.175 mg/ml and were administered i.p. at a dose of 0.175 mg/kg. NAP was prepared at 0.1 mg/1.3 ml in saline (0.9% NaCl) and about 0.1 ml was injected subcutaneously to a ~300 g rat to achieve a dose of 25 microgram/kg (exact calculations were made based on the daily body weights). For 2.5 microgram/kg, the injection solution was diluted by 10 and again 0.1 ml was injected per rat. Treatments took place daily (5 days a week) for ~3 weeks (20 days) with the dosage calculated on daily body weight. NAP was administered at the same time as the vincristine, in the dosage and the amount where indicated the following schedule.

Four groups were evaluated: 1) Control, saline (n=10), 2) Vincristine (i.p.) 0.175 mg/kg (n=10), 3) Vincristine (i.p.) 0.175 mg/kg+NAP (s.c.) 2.5 microgram/kg (n=10), and 4) Vincristine (i.p.) 0.175 mg/kg+NAP (s.c.) 25 microgram/kg (n=10).

After a week cessation of treatment, a final boost of vincristine was given i.p. daily for three days and NAP at 25 microgram/kg was given intranasally to group number 4 only. The intranasal formulation followed previous experiment (7.5 mg Sodium Chloride, 1.7 mg Citric Acid Monohydrate, 3.0 mg Disodium Phosphate Dihydrate, 0.2 mg Benzalkonium Chloride Solution (50%) per 1 mL Sterile Water (U.S.P.) Alcalay et al., infra). For behavioral testing baseline toxin effects were evaluated 2-23 days following the first injection, using the testing procedures below:

1) Rota-Rod

Vincristine treated animals show impaired performance on the rota-rod test which evaluates muscle innervation and strength (Boyle et al., *J Pharmacol Exp Ther* 279: 410-415 (1996)) Here, the rota-rod test was performed on days 3, 8, 15 and 23 after the initiation of the vincristine injections.

In the Rota-rod test a rodent is placed on a rotating rod. The speed of rotation is gradually increased and the rodent's ability to remain on the rotating rod is recorded. Here, the speed was gradually increased from 3-30 rpm every 30 seconds with 3 rpm increments up to 200 seconds. The time spent on the rota-rod without falling was recorded. Impaired animals fall earlier from the rota-rod. The time spent by each animal in a single treatment group was summed for all treatment and test days as seen on FIG. 1. Statistical analysis showed a significant difference between the vincristine treated animals and the control animals indicating impairment in the vincristine animals ($P<0.01$). Group 3 treatment with NAP (2.5 microgram/kg) significantly improved the performance similar to control values Animals treated with NAP (25 micrograms/kg) in group 4 showed no significant difference from animals treated with vincristine treated alone and were significantly different from controls.

2) Motor Evaluation

Motor examination was performed on days 6, 9, 13 and 24 after the initiation of the vincristine injections. Rats were examined after vincristine injection, with the use of a motor disability scale. (Bederson J B, et al., *Stroke*. 1986; 17: 472-476; Leker R R, et al., *J Neurol Sci*. 1999; 162: 114-119).

Animals were assessed based on their failure to walk out of a circle 30 cm in diameter within 20 seconds.

Figure 2:
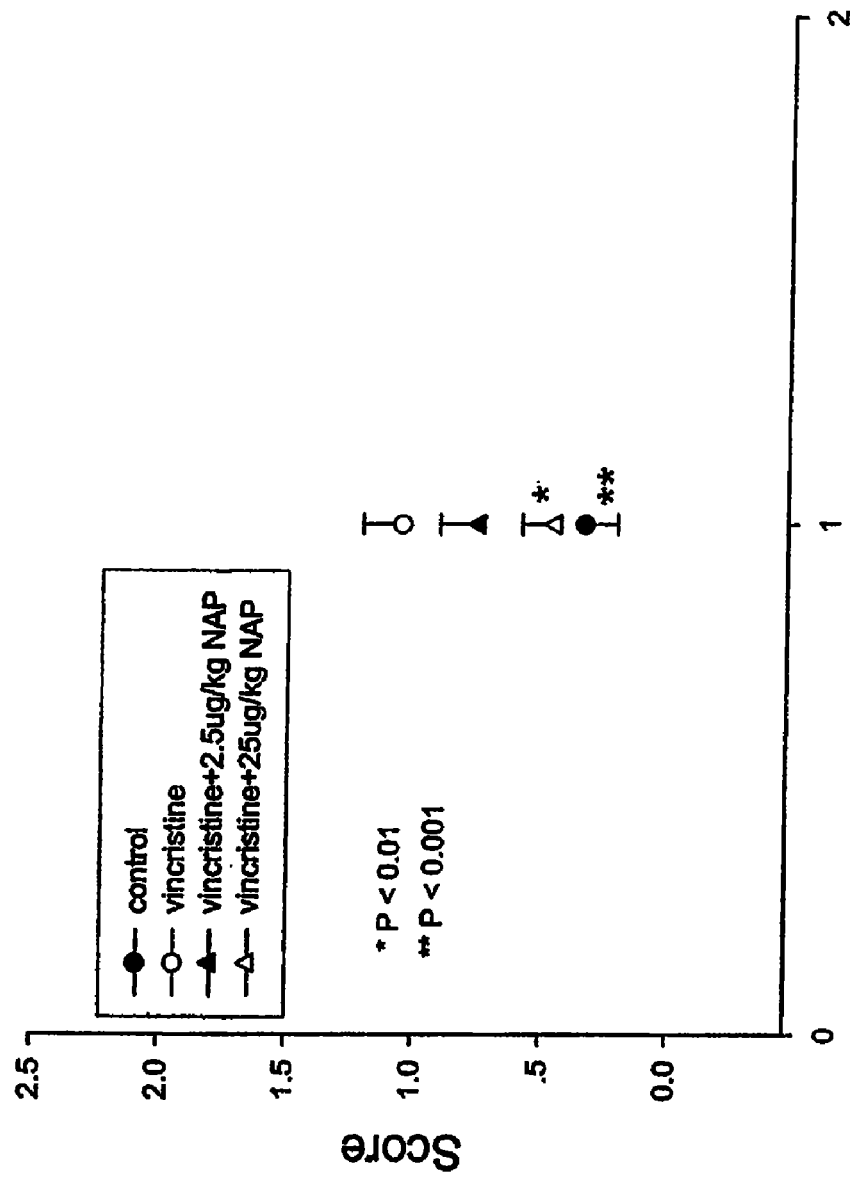
FIG. 2: Motor evaluations: The ability to exit a circle 30 cm in diameter within 20 seconds. Vincristine-treated rats (n=10) are significantly worse as compared to control animals (n=10) (P<0.001). Treatment with NAP (25 microgram/kg) (n=10) significantly improved the performance similar to control values (P<0.01).

FIG. 2 shows the results of motor evaluations. The ability to exit a 30 cm in diameter within 20 seconds was significantly reduced for vincristine-treated rats as compared to control animals ($P<0.001$). Additional treatment with NAP (25 microgram/kg) in group 4 significantly improved the performance similar to control values ($P<0.01$). Animals treated with NAP (2.5 micrograms/kg) in group 3 showed no significant difference from animals treated with vincristine alone.

3) Olfactory Discrimination Test

Treatments took place daily (5 days a week) for ~3 weeks (20 days) with the dosage calculated on daily body weight. NAP was administered subcutaneously at the same time as the vincristine was administered intraperitoneally, in the dosage and the amount indicated in the schedule above. After a week cessation of treatment a final boost of vincristine was given i.p. daily for three days and NAP at 25 microgram/kg was given intranasally to group number 4 only. The intranasal formulation followed the previous experiment (Alcalay et al., infra). An olfactory discrimination test was performed on each of the three days of NAP treatment during the final boost period. (Macknin et al., *Brain Res*. 1000, 174-78 (2004)) The odors tested were 1) Deionized water (ddw) and 2) Scented extracts, i.e., vanilla/almond.

Overall the experiment included 3 odors (water and two scented extracts) each encompassing 3 trials of 2 minutes. New dipped tip was introduced at the beginning of each trial for the different scents.

Thirty minutes before the testing the subjects were housed in separate cages and a cotton tip dipped in water was placed hanging into the cage. During these 30 minutes the animal was acclimatized to the tip and the cage. Thereafter, the cotton tip was dipped in the desired scent and placed hanging from the top of the cage.

The duration (seconds) of tip sniffing with count starting when the nose of the animal is approximately 1 cm. from the tip and stopping when the animal places its paws on the tip or tries to bite it reflects olfactory responses.

If the animal can discriminate odors, then each trial of the same scent it will be less and less interested—thus the sniffing time will go down. But when the odor is replaced by a new one—the sniffing time will increase.

T-test was used to make comparisons of individual test groups with control group or between unpaired groups.

Figure 3:
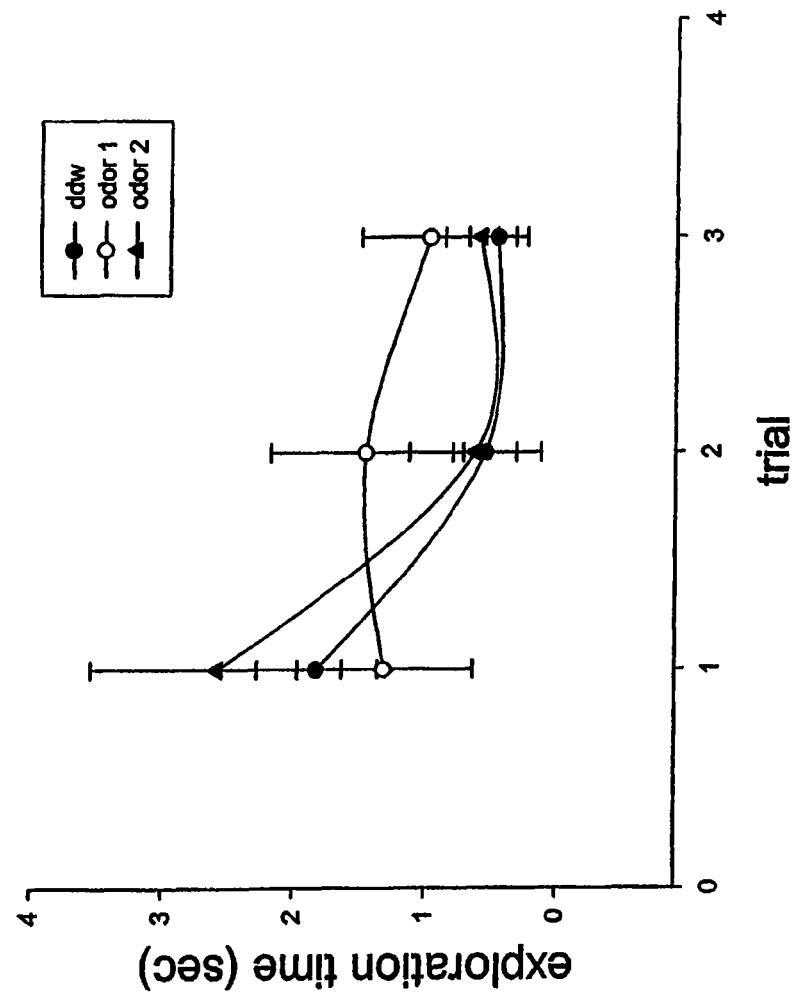
FIGS. 3, 4 and 5: Time spent with new odors: olfaction capacity. The time spent with each odor over the three consecutive tests was recorded.
Figure 4:
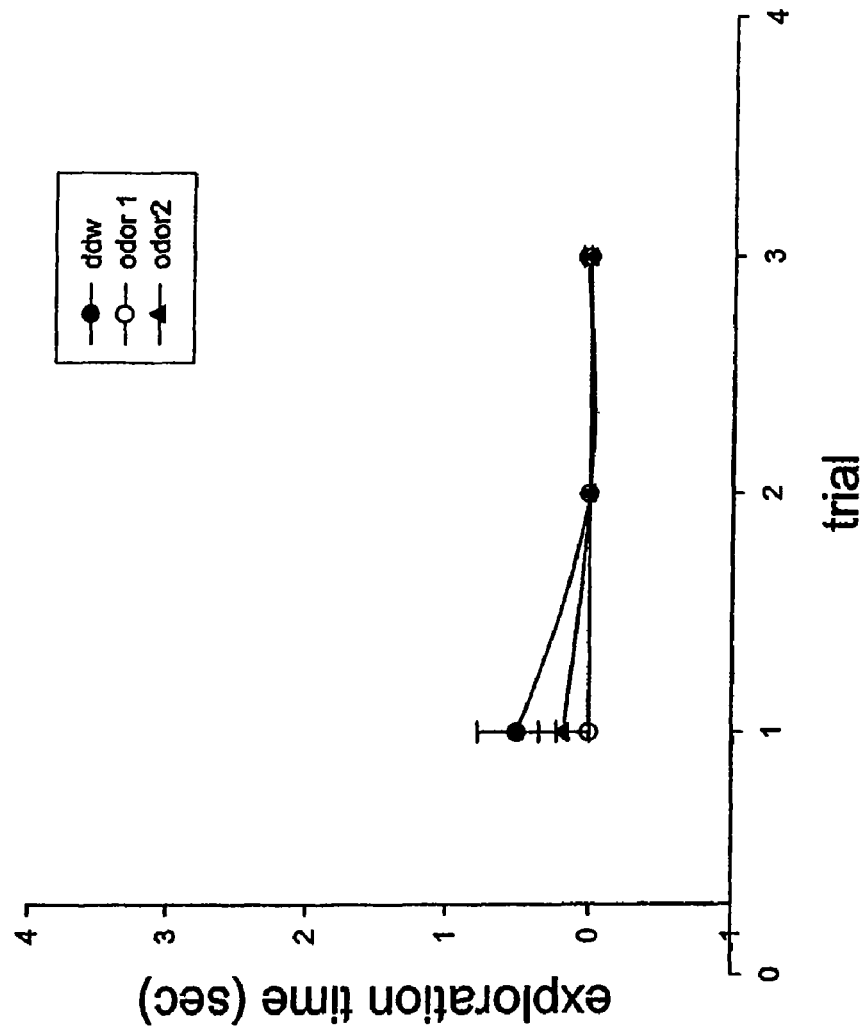
Figure 5:
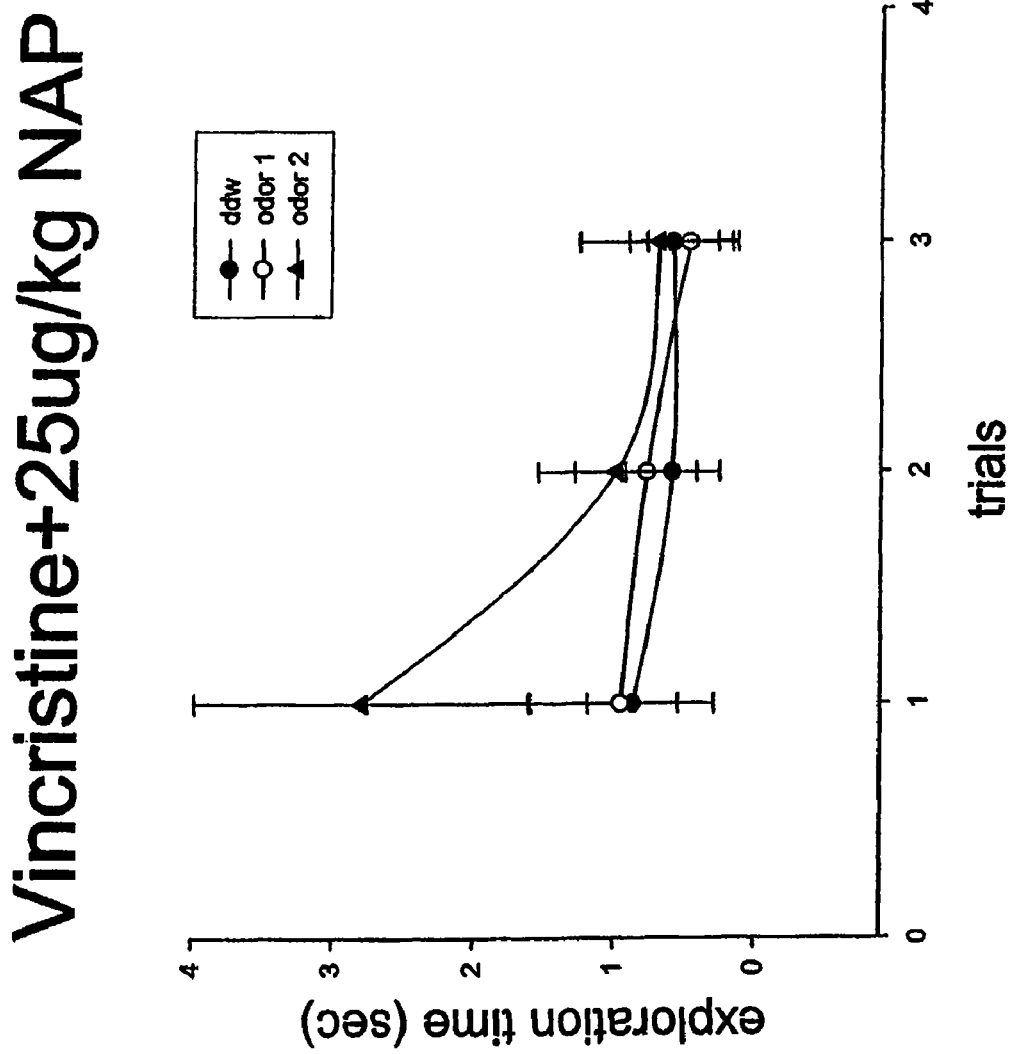

FIGS. 3-5 show the time spent with new odors, i.e., olfaction capacity. The time spent with each odor over the three consecutive tests was recorded. FIG. 3, for control rats (Group 1), FIG. 4 for vincristine treated rats (Group 2) and FIG. 5 for vincristine and 25 microgram/kg NAP treated rats (Group 4). While the Group 2 vincristine-treated rats did not show any initial interest in the new smell, a trend toward increased interest toward a new odor was observed in the control and the vincristine-NAP treated rats. These results were further evaluated in FIG. 6.

Figure 6:
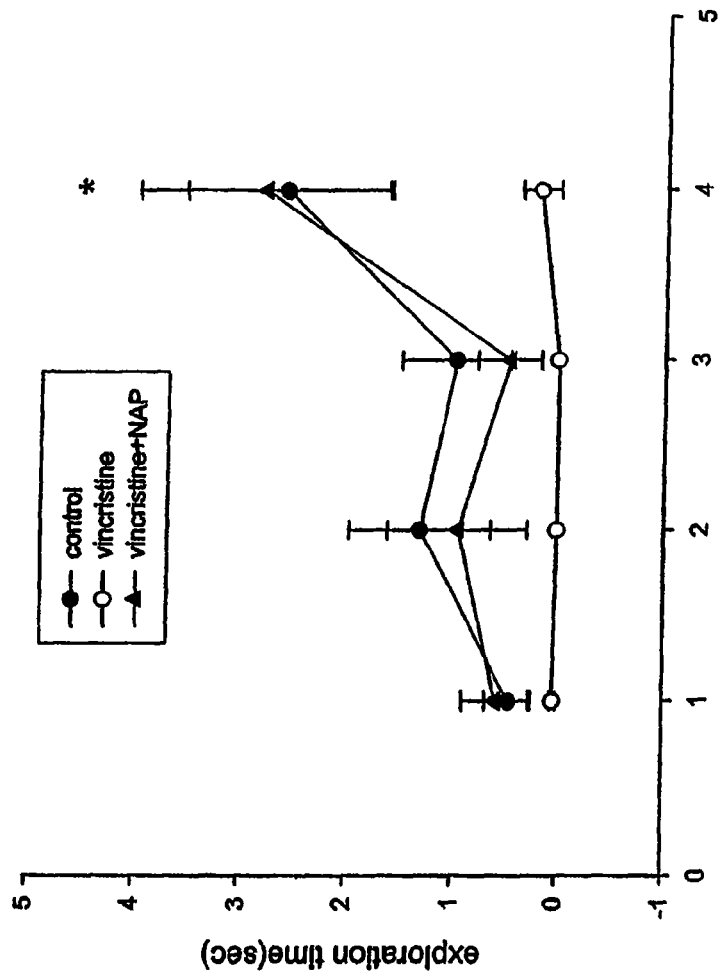
FIG. 6: Comparison between time periods spent with a certain odor after exchanging for a former scent-odor discrimination test: The figure depicts 4 points, point 1=water (ddw) trial 3; point 2=odor #1, trial #1; point 3=odor #1, trial 3; point 4=odor #2, trial 1. Results showed a significant difference in the time taken to sniff the third odor when comparing control to vincristine-treated rats or vincristine-treated rats with vincristine+25 microgram/kg NAP (P<0.05).

FIG. 6 shows a comparison between time periods spent with a certain odor after exchanging for a new scent-odor discrimination test: The figure depicts 4 points, point 1=water (ddw) trial 3; point 2=odor #1, trial #1; point 3=odor #1, trial 3; point 4=odor #2, trial 1. Results showed a significant difference in the time taken to sniff the third odor when comparing vincristine-treated rats (Group 2) to either control rats (Group 1) or to vincristine+25 microgram/kg NAP rats (Group 4) (P<0.05).

Results

The result of these three independent tests evaluating peripheral neurotoxicity, specifically muscle innervation or strength (e.g. rota-rod test); Motor abilities (movement and circle exit); and behavioral/olfaction abilities, indicates that treatment of animals with NAP significantly reduced impairment and evidence of peripheral neurotoxicity that results from vincristine treatment.

The results of the olfaction experiment in particular demonstrates that intranasal NAP provides a benefit to animals that lose olfaction capacity as a result of chemotherapy. This supports the finding that measurement of olfaction capacity can be used to determine whether subjects are responding to ADNF polypeptide treatment, either for neurodegenerative disease or peripheral neurotoxicity, by measuring whether the progress of hyposmia or anosmia has been halted, reduced or reversed in patients receiving treatment with ADNF polypeptides.

Example 2

Administration of NAP Reduces Neurotoxicity Induced by Chemotherapeutic Agents

Aim of the study: The aim of the present randomized blind study is to investigate the efficacy of NAP in reducing neurotoxicity induced by the chemotherapeutic agent vincristine in men and women with advanced carcinoma.

Methods:

Initially 21 patients with advanced carcinoma are randomized between groups A and B. In group A (11 patients) NAP is administered at a dose of 15 mg/45-70 kg before vincristine infusion (1.4 mg/m$^2$). In group B (10 patients) the same chemotherapeutic protocol is followed without administration of NAP. Before beginning of chemotherapy and after 6 chemotherapeutic cycles all patients will undergo clinical neurologic examination and nerve conduction study by a neurologist who is blind to the randomization.

Results:

Clinical neurologic examination is assessed neurotoxicity indicators such as tendon reflexes, superficial sensory perception and muscle strength, as well as neuropathic symptoms. Nerve conduction study assesses nerve conduction velocity and action potential amplitude in 7 peripheral nerves. Deterioration of nerve conduction parameters, tendon reflexes, muscle strength, superficial sensory perception, but also of patient's symptoms is significantly more severe in group B.

Conclusion:

Concurrent NAP administration will be found to significantly reduce neurotoxicity induced by the chemotherapeutic agent vincristine in men and women with advanced carcinoma.

Example 3

Randomized Trial with or without NAP to Reduce Neurotoxicity Side Effects Under Chemotherapy with Oxaliplatin (L-OHP), FA/5-FU Aim of the study: Chemotherapy with L-OHP, FA, 5-FU has a high activity in advanced colorectal cancer (ACRC). The main dose-limiting toxicity of chemotherapy with L-OHP is a peripheral sensory neuropathy. In this study the patients (pts) will receive a chemotherapy with L-OHP, FA and 5-FU with or without NAP. The question is whether a reduction of side effects of neurotoxicity is seen after application of NAP.

Materials and Methods

We include 27 patients with ACRC. In arm A chemotherapy is applied with L-OHP 85 mg/m2 d1, FA 500 mg/m2 d1+d2 and 5-FU 4000 mg/m2 over 48 h continuous infusion as biweekly schedule. In arm B, 15 mg/45-70 kg NAP is given over 10 min i.v. before application of the same schedule of chemotherapy. Investigation of toxicity, neurological examination and a blood count is performed before every cycle. For a daily documentation of the side effects every patient receives a questionnaire. The NAP group shows a significant reduction of peripheral neurotoxicity. In the NAP group grade II/III leucopenia occurs at a lower frequency than in the control group.

Conclusion

Side effects such as peripheral neurotoxicity under chemotherapy including L-OHP, FA/5-FU will be reduced under supportive care with NAP.

Example 4

Taxol Neurotoxicity and Protection by NAP

The present study was designed to evaluate whether NAP treatment successfully reduced peripheral neurotoxicity induced by the taxane taxol in rats.

Methods

Experiment 1

Forty Sprague-Dawley rats (eight weeks old) were divided into four groups that received the following treatments: a) 10% Cremophor EL in Saline; b) taxol for a cumulative dose of 5.6 mg/kg; c) taxol for a cumulative dose of 5.6 mg/kg+ NAP 2.5 µg/kg/Day; or d) taxol for a cumulative dose of 5.6 mg/kg+NAP 25 µg/kg/Day. The taxol was reconstituted in a vehicle of 10% Cremophor EL in Saline.

Taxol treatments were administered four times intraperitoneally (i.p.) on nonconsecutive days in a volume of 250 µl each time. NAP was administered daily on 8 consecutive days from the first day of taxol injection (with a 2 day brake on the weekend).

Rats were tested in the rota-rod and plantar test. The rota-rod test is described above and assesses muscle strength. The plantar test evaluates thermal hyperalgesia. For the plantar test, each rat was placed in a clear plastic chamber with a plastic floor and allowed a short period to acclimatize to the new environment (approximately 2-5 min). The animals were then challenged with a radiant Infrared (IR) heat source directed at the plantar surface of the hind paw from below (7371 Plantar Test, Ugo Basile). The withdrawal latency of both the ipsilateral and contralateral hind paw was evaluated. The infrared intensity was set at IR55 and the maximum length of exposure to the IR source was eighteen seconds. Statistical differences were tested by ANOVA and by t-test.

Figure 7:
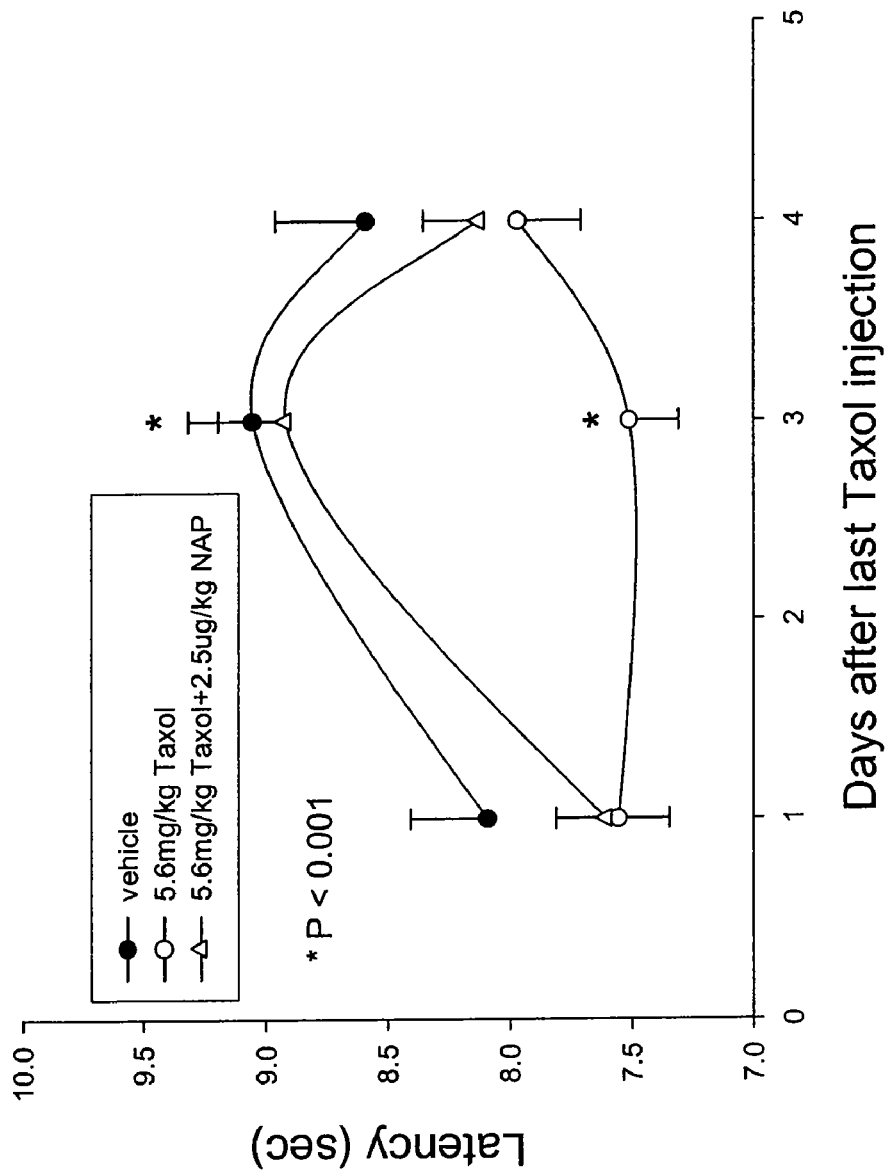
FIG. 7: Plantar tests were performed on rats receiving a total dose of 5.6 mg/kg taxol, and similar rats receiving taxol plus 2.5 µg/kg/day NAP. The plantar test shows taxol and 2.5 µg/kg/day NAP treated animals (n=10) perform better than taxol treated alone (n=10). (*p<0.01).

Results:

A statistically significant difference between groups was observed only in the plantar test and results are shown in FIG. 7. After the last taxol injection on day three, the taxol-treated rats exhibited thermal hyperalgesia, which was ameliorated by 2.5 µg/kg/day NAP injections. 25 ug/kg NAP did not affect the plantar test. The hyperalgesia induced by the taxol treatment diminished after 4 days. Rota-rod experiments did not show statistically significant differences between groups in this experiment.

Experiment 2

Fifteen Sprague-Dawley Rats (seven weeks old) were randomly divided into three groups that received the following treatments: a) 10% Cremophor EL in Saline; b) taxol for a cumulative dose of 9 mg/kg; or c) taxol for a cumulative dose of 9 mg/kg+2.5 μg/kg/Day NAP. The taxol was reconstituted in a vehicle of 10% Cremophor EL in Saline.

Taxol was administered twice on nonconsecutive days; each rat received 0.4-0.5 ml Taxol solution (i.p.). NAP was administered in 0.1 ml volume for five consecutive days starting with first injection of Taxol.

The rats were tested a day after the last Taxol injection on rota-rod and plantar tests as described above. Statistical significance was only observed using non-paired, one tail t-test.

Results

Figure 8:
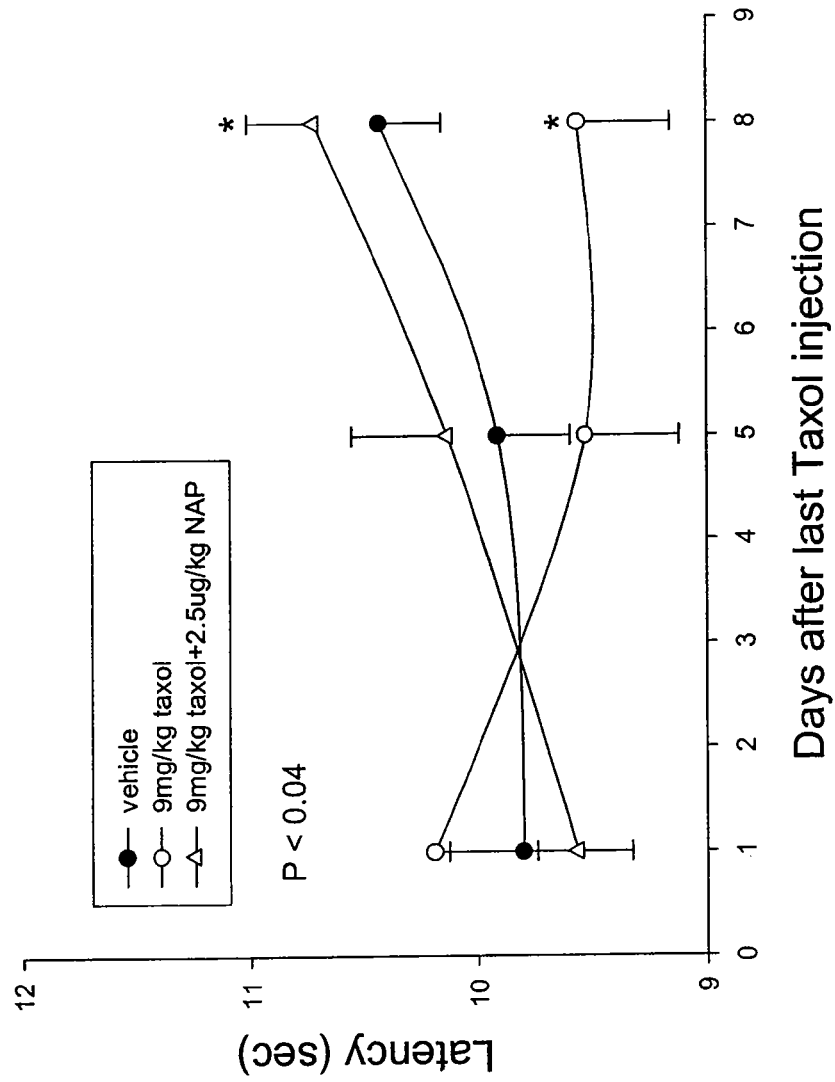
FIG. 8: Plantar tests were performed on rats receiving a total dose of 9 mg/kg taxol, and similar rats receiving taxol plus 2.5 µg/kg/day NAP. The plantar test shows taxol and 2.5 µg/kg/day NAP treated animals (n=10) perform better than taxol treated alone (n=5). (*p<0.04).
Figure 9:
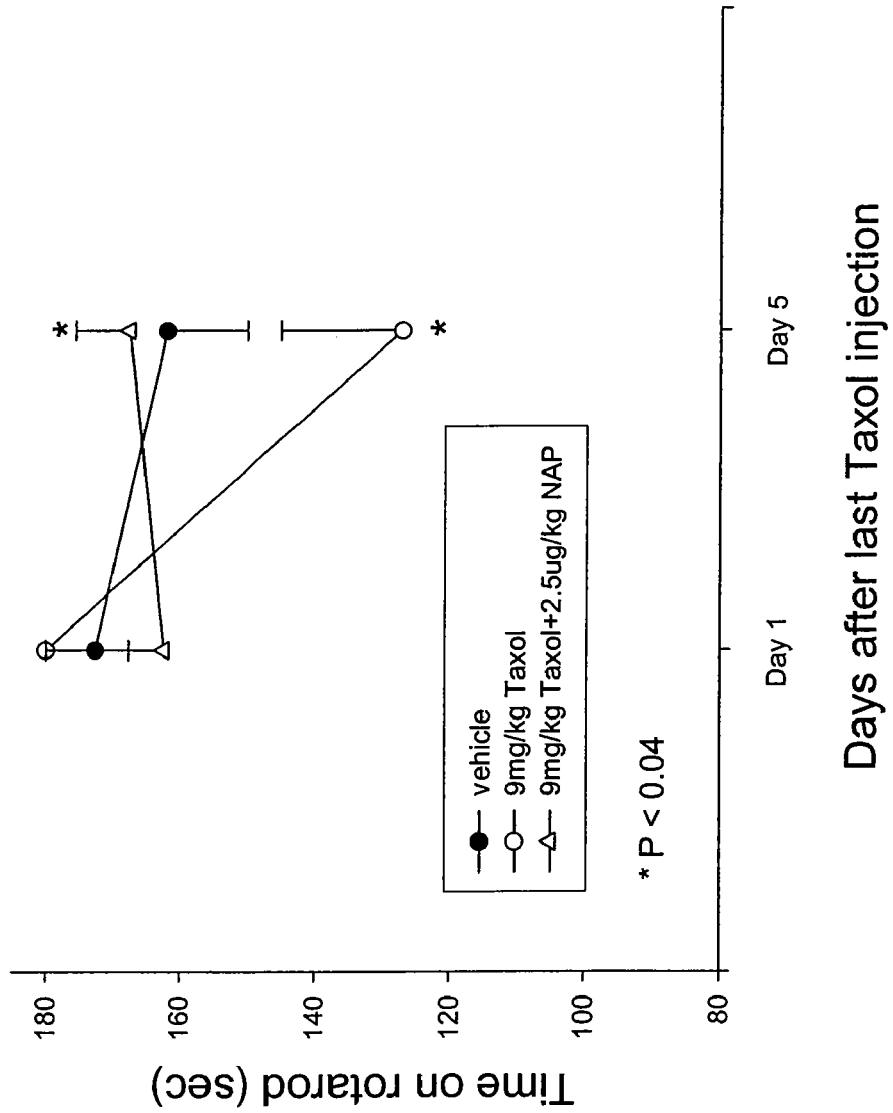
FIG. 9: Rotarod tests were performed on rats receiving a total dose of 9 mg/kg taxol, and similar rats receiving taxol plus 2.5 µg/kg/day NAP. The rotarod test shows taxol and 2.5 µg/kg/day NAP treated animals (n=5) perform better than taxol treated alone (n=10). (*p<0.04).

Results are shown in FIG. 8 (Plantar test) and FIG. 9 (Rota-rod test). Taxol-treated rats exhibited a significant thermal hyperalgesia eight days after the last Taxol injection. The hyperalgesia was ameliorated by NAP treatment. At this higher dose of Taxol, a significant effect on neuromuscular function was measured using the rota-rod test five days after the first taxol injection. The neuromuscular effect was ameliorated by NAP treatment.

Conclusion:

NAP protects against Taxol-induced neuropathy in vivo.

The examples set out above are intended to be exemplary of the effects of the invention, and are not intended to limit the embodiments or scope of the invention contemplated by the claims set out below. Other variants of the invention will be readily apparent to one of ordinary skill in the art and are encompassed by the appended claims. All publications, databases, Genbank sequences, GO terms, patents, and patent applications cited herein are hereby incorporated by reference.

What is claimed is:

1. A method for the treatment of cancer or neoplasia with reduced peripheral neurotoxicity, the method comprising
   a) administering an anti-cancer agent to a subject in need thereof; and
   b) administering, contemporaneously or sequentially with the anti-cancer agent of step a), an ADNF polypeptide in an effective amount in a pharmaceutically acceptable carrier, thereby reducing peripheral neurotoxicity associated with the anti-cancer agent, wherein the ADNF polypeptide is a member selected from the group consisting of:
   (i) an ADNF I polypeptide comprising an active core site having the amino acid sequence of Ser-Ala-Leu-Leu-Arg-Ser-Ile-Pro-Ala (SEQ ID NO:1), wherein at least one amino acid in SEQ ID NO:1 is optionally a D-amino acid;
   (ii) an ADNF III polypeptide comprising an active core site having the amino acid sequence of Asn-Ala-Pro-Val-Ser-Ile-Pro-Gln (SEQ ID NO:2), wherein at least one amino acid in SEQ ID NO:2 is optionally a D-amino acid; and
   (iii) a mixture of the ADNF I polypeptide of part (i) and the ADNF III polypeptide of part (ii).

2. The method of claim 1, wherein said anti-cancer agent is a vinca alkaloid.

3. The method of claim 1, wherein the ADNF polypeptide is a member selected from the group consisting of a full length ADNF I polypeptide, a full length ADNF III polypeptide (ADNP), and a mixture of a full length ADNF I polypeptide and a full length ADNF III polypeptide.

4. The method of claim 1, wherein the ADNF polypeptide is an ADNF I polypeptide of part (i).

5. The method of claim 1, wherein the active core site of the ADNF polypeptide comprises at least one D-amino acid.

6. The method of claim 1, wherein the ADNF I polypeptide has the formula $(R^1)_x$-Ser-Ala-Leu-Leu-Arg-Ser-Ile-Pro-Ala-$(R^2)_y$ (SEQ ID NO:20), in which
   $R^1$ is an amino acid sequence comprising from 1 to about 40 amino acids wherein each amino acid is independently selected from the group consisting of naturally occurring amino acids and amino acid analogs;
   $R^2$ is an amino acid sequence comprising from 1 to about 40 amino acids wherein each amino acid is independently selected from the group consisting of naturally occurring amino acids and amino acid analogs; and
   x and y are independently selected and are equal to zero or one.

7. The method of claim 6, wherein the ADNF I polypeptide is Ser-Ala-Leu-Leu-Arg-Ser-Ile-Pro-Ala (SEQ ID NO:1).

8. The method of claim 6, wherein the ADNF I polypeptide is selected from the group consisting of:

```
                                            (SEQ ID NO: 3)
Val-Leu-Gly-Gly-Gly-Ser-Ala-Leu-Leu-Arg-Ser-Ile-
Pro-Ala;

(SEQ ID NO: 4)
Val-Glu-Glu-Gly-Ile-Val-Leu-Gly-Gly-Gly-Ser-Ala-
Leu-Leu-Arg-Ser-Ile-Pro-Ala;

(SEQ ID NO: 5)
Leu-Gly-Gly-Gly-Ser-Ala-Leu-Leu-Arg-Ser-Ile-Pro-
Ala;

(SEQ ID NO: 6)
Gly-Gly-Gly-Ser-Ala-Leu-Leu-Arg-Ser-Ile-Pro-Ala;

(SEQ ID NO: 7)
Gly-Gly-Ser-Ala-Leu-Leu-Arg-Ser-Ile-Pro-Ala;

(SEQ ID NO: 8)
Gly-Ser-Ala-Leu-Leu-Arg-Ser-Ile-Pro-Ala;
and (SEQ ID NO: 1)
Ser-Ala-Leu-Leu-Arg-Ser-Ile-Pro-Ala.
```

9. The method of claim 6, wherein the ADNF I polypeptide comprises up to about 20 amino acids at either or both of the N-terminus and the C-terminus of the active core site.

10. The method of claim 1, wherein the ADNF polypeptide is an ADNF III polypeptide of part (ii).

11. The method of claim 10, wherein the ADNF III polypeptide has the formula $(R^1)_x$-Asn-Ala-Pro-Val-Ser-Ile-Pro-Gln-$(R^2)_y$ (SEQ ID NO:13), in which
   $R^1$ is an amino acid sequence comprising from 1 to about 40 amino acids wherein each amino acid is independently selected from the group consisting of naturally occurring amino acids and amino acid analogs;
   $R^2$ is an amino acid sequence comprising from 1 to about 40 amino acids wherein each amino acid is independently selected from the group consisting of naturally occurring amino acids and amino acid analogs; and
   x and y are independently selected and are equal to zero or one.

12. The method of claim 10, wherein the ADNF III polypeptide is Asn-Ala-Pro-Val-Ser-Ile-Pro-Gln (SEQ ID NO:2).

13. The method of claim 10, wherein the active core site of the ADNF III polypeptide comprises at least one D-amino acid.

14. The method of claim 10, wherein the ADNF III polypeptide is a member selected from the group consisting of:

```
                                            (SEQ ID NO: 9)
Gly-Gly-Asn-Ala-Pro-Val-Ser-Ile-Pro-Gln;

(SEQ ID NO: 10)
Leu-Gly-Gly-Asn-Ala-Pro-Val-Ser-Ile-Pro-Gln-Gln-
Ser;

(SEQ ID NO: 11)
Leu-Gly-Leu-Gly-Gly-Asn-Ala-Pro-Val-Ser-Ile-Pro-
Gln-Gln-Ser;

(SEQ ID NO: 12)
Ser-Val-Arg-Leu-Gly-Leu-Gly-Gly-Asn-Ala-Pro-Val-
Ser-Ile-Pro-Gln-Gln-Ser;
and (SEQ ID NO: 2)
Asn-Ala-Pro-Val-Ser-Ile-Pro-Gln.
```

15. The method of claim 10, wherein the ADNF III polypeptide comprises up to about 20 amino acids at either or both of the N-terminus and the C-terminus of the active core site.

16. The method of claim 1, wherein a mixture of the ADNF I polypeptide of part (i) and the ADNF III polypeptide of part (ii) is administered to the subject.

17. The method of claim 16, wherein either or both active core sites of the ADNF I polypeptide and the ADNF III polypeptide comprise at least one D-amino acid.

18. The method of claim 16, wherein the ADNF I polypeptide is Ser-Ala-Leu-Leu-Arg-Ser-Ile-Pro-Ala (SEQ ID NO:1), and wherein the ADNF III polypeptide is Asn-Ala-Pro-Val-Ser-Ile-Pro-Gln (SEQ ID NO:2).

19. The method of claim 16, wherein the ADNF I polypeptide is a member selected from the group consisting of:

(SEQ ID NO: 3)
Val-Leu-Gly-Gly-Gly-Ser-Ala-Leu-Leu-Arg-Ser-Ile-Pro-Ala;

(SEQ ID NO: 4)
Val-Glu-Glu-Gly-Ile-Val-Leu-Gly-Gly-Gly-Ser-Ala-Leu-Leu-Arg-Ser-Ile-Pro-Ala;

(SEQ ID NO: 5)
Leu-Gly-Gly-Gly-Ser-Ala-Leu-Leu-Arg-Ser-Ile-Pro-Ala;

(SEQ ID NO: 6)
Gly-Gly-Gly-Ser-Ala-Leu-Leu-Arg-Ser-Ile-Pro-Ala;

(SEQ ID NO: 7)
Gly-Gly-Ser-Ala-Leu-Leu-Arg-Ser-Ile-Pro-Ala;

(SEQ ID NO: 8)
Gly-Ser-Ala-Leu-Leu-Arg-Ser-Ile-Pro-Ala;
and (SEQ ID NO: 1)
Ser-Ala-Leu-Leu-Arg-Ser-Ile-Pro-Ala;
and wherein the ADNF III polypeptide is selected from the group consisting of:

(SEQ ID NO: 9)
Gly-Gly-Asn-Ala-Pro-Val-Ser-Ile-Pro-Gln;

(SEQ ID NO: 10)
Leu-Gly-Gly-Asn-Ala-Pro-Val-Ser-Ile-Pro-Gln-Gln-Ser;

(SEQ ID NO: 11)
Leu-Gly-Leu-Gly-Gly-Asn-Ala-Pro-Val-Ser-Ile-Pro-Gln-Gln-Ser;

(SEQ ID NO: 12)
Ser-Val-Arg-Leu-Gly-Leu-Gly-Gly-Asn-Ala-Pro-Val-Ser-Ile-Pro-Gln-Gln-Ser;
and (SEQ ID NO: 2)
Asn-Ala-Pro-Val-Ser-Ile-Pro-Gln.

20. The method of claim 16, wherein the ADNF I polypeptide comprises up to about 20 amino acids at either or both of the N-terminus and the C-terminus of the active core site of the ADNF I polypeptide, and wherein the ADNF III polypeptide comprises up to about 20 amino acids at either or both of the N-terminus and the C-terminus of the active core site of the ADNF III polypeptide.

21. The method of claim 1, wherein the ADNF polypeptide is administered intranasally, orally, intravenously or subcutaneously.

* * * * *

```
                          SEQUENCE LISTING

<160> NUMBER OF SEQ ID NOS: 21

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:activity
      dependent neurotrophic factor I (ADNF I) active
      core site (SAL, ADNF-9)

<400> SEQUENCE: 1

Ser Ala Leu Leu Arg Ser Ile Pro Ala
 1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:activity
      dependent neurotrophic factor III (ADNF III,
      activity-dependent neuroprotective protein (ADNP))
      active core site (NAP)

<400> SEQUENCE: 2

Asn Ala Pro Val Ser Ile Pro Gln
 1               5

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 3

Val Leu Gly Gly Gly Ser Ala Leu Leu Arg Ser Ile Pro Ala
 1               5                  10

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence:ADNF I
      polypeptide
```

```
<400> SEQUENCE: 4

Val Glu Glu Gly Ile Val Leu Gly Gly Gly Ser Ala Leu Leu Arg Ser
 1               5                  10                  15

Ile Pro Ala

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 5

Leu Gly Gly Gly Ser Ala Leu Leu Arg Ser Ile Pro Ala
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 6

Gly Gly Gly Ser Ala Leu Leu Arg Ser Ile Pro Ala
 1               5                  10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 7

Gly Gly Ser Ala Leu Leu Arg Ser Ile Pro Ala
 1               5                  10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 8

Gly Ser Ala Leu Leu Arg Ser Ile Pro Ala
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 9

Gly Gly Asn Ala Pro Val Ser Ile Pro Gln
 1               5                  10

<210> SEQ ID NO 10
<211> LENGTH: 13
```

```
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 10

Leu Gly Gly Asn Ala Pro Val Ser Ile Pro Gln Gln Ser
 1               5                  10

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 11

Leu Gly Leu Gly Gly Asn Ala Pro Val Ser Ile Pro Gln Gln Ser
 1               5                  10                  15

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 12

Ser Val Arg Leu Gly Leu Gly Gly Asn Ala Pro Val Ser Ile Pro Gln
 1               5                  10                  15

Gln Ser

<210> SEQ ID NO 13
<211> LENGTH: 88
<212> TYPE: PRT
<213> ORGANISM: Artificial Sequence
<220> FEATURE:
<223> OTHER INFORMATION: Description of Artificial Sequence:ADNF III
      polypeptide, NAP related peptide
<220> FEATURE:
<221> NAME/KEY: MOD_RES
<222> LOCATION: (1)..(40)
<223> OTHER INFORMATION: Xaa = any naturally occurring amino acid or
      amino acid analogue, Xaa at positions 1-40 may be present
      or absent
<220> FEATURE:
<221> NAME/KEY: MOD_RES
<222> LOCATION: (49)..(88)
<223> OTHER INFORMATION: Xaa = any naturally occurring amino acid or
      amino acid analogue, Xaa at positions 49-88 may be present
      or absent

<400> SEQUENCE: 13

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asn Ala Pro Val Ser Ile Pro Gln
        35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa
```

```
<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:1-R or 2-R
      within the formula for ADNF I polypeptide

<400> SEQUENCE: 14

Val Leu Gly Gly Gly
  1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:2-R within
      the formula for ADNF I polypeptide

<400> SEQUENCE: 15

Val Leu Gly Gly
  1

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:2-R within
      the formula for ADNF I polypeptide

<400> SEQUENCE: 16

Val Leu Gly Gly Val
  1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:2-R within
      the formula for ADNF I polypeptide

<400> SEQUENCE: 17

Gly Val Leu Gly Gly
  1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence:1-R within
      the formula for ADNF III polypeptide

<400> SEQUENCE: 18

Leu Gly Leu Gly Gly
  1               5
```

```
<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence:1-R within
      the formula for ADNF III polypeptide

<400> SEQUENCE: 19

Ser Val Arg Leu Gly Leu Gly Gly
 1               5

<210> SEQ ID NO 20
<211> LENGTH: 89
<212> TYPE: PRT
<213> ORGANISM: Artificial Sequence
<220> FEATURE:
<223> OTHER INFORMATION: Description of Artificial Sequence:ADNF I
      polypeptide, SAL related peptide
<220> FEATURE:
<221> NAME/KEY: MOD_RES
<222> LOCATION: (1)..(40)
<223> OTHER INFORMATION: Xaa = any naturally occurring amino acid or
      amino acid analogue, Xaa at positions 1-40 may be present
      or absent
<220> FEATURE:
<221> NAME/KEY: MOD_RES
<222> LOCATION: (50)..(89)
<223> OTHER INFORMATION: Xaa = any naturally occurring amino acid or
      amino acid analogue, Xaa at positions 50-89 may be present
      or absent

<400> SEQUENCE: 20

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Ser Ala Leu Leu Arg Ser Ile Pro
        35                  40                  45

Ala Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa
                85

<210> SEQ ID NO 21
<211> LENGTH: 26
<212> TYPE: PRT
<213> ORGANISM: Artificial Sequence
<220> FEATURE:
<223> OTHER INFORMATION: Description of Artificial Sequence:ADNF
      polypeptide, SAL related peptide, Colivelin combination of SAL
      active site and derivative of Humanin protein
      AGA-(C8R)HNG17

<400> SEQUENCE: 21

Ser Ala Leu Leu Arg Ser Ile Pro Ala Pro Ala Gly Ala Ser Arg Leu
 1               5                  10                  15

Leu Leu Leu Thr Gly Glu Ile Asp Leu Pro
            20                  25
```